(12) United States Patent
Johnston et al.

(10) Patent No.: US 7,255,693 B1
(45) Date of Patent: Aug. 14, 2007

(54) HEATED CATHETER USED IN CRYOTHERAPY

(75) Inventors: Mark H. Johnston, Rockville, MD (US); Jennifer B. Cartledge, Clemson, SC (US)

(73) Assignee: CSA Medical, Inc., Lutherville, MD (US)

( * ) Notice: Subject to any disclaimer, the term of this patent is extended or adjusted under 35 U.S.C. 154(b) by 0 days.

(21) Appl. No.: 10/352,266

(22) Filed: Jan. 27, 2003

Related U.S. Application Data

(63) Continuation-in-part of application No. 10/106,985, filed on Mar. 26, 2002, now Pat. No. 7,025,762, which is a continuation-in-part of application No. 09/477,839, filed on Jan. 5, 2000, now Pat. No. 6,383,181, which is a continuation-in-part of application No. 09/050,150, filed on Mar. 30, 1998, now Pat. No. 6,027,499.

(60) Provisional application No. 60/047,484, filed on May 23, 1997.

(51) Int. Cl.
*A61B 18/02* (2006.01)

(52) U.S. Cl. .......................... 606/24; 606/20

(58) Field of Classification Search ............ 606/20–24; 128/898
See application file for complete search history.

(56) References Cited

U.S. PATENT DOCUMENTS

| | | | |
|---|---|---|---|
| 3,298,371 A | 1/1967 | Lee | 128/303.1 |
| 3,507,283 A | 4/1970 | Thomas, Jr. | 128/303.1 |
| 3,651,813 A * | 3/1972 | Bryne | 128/200.14 |
| 4,202,336 A * | 5/1980 | van Gerven | 606/21 |
| 4,654,024 A * | 3/1987 | Crittenden et al. | 606/28 |
| 4,946,460 A * | 8/1990 | Merry et al. | 606/24 |
| 5,035,694 A * | 7/1991 | Kasprzyk et al. | 606/27 |
| 5,047,025 A * | 9/1991 | Taylor et al. | 606/31 |
| 5,057,106 A * | 10/1991 | Kasevich et al. | 606/33 |
| 5,275,595 A * | 1/1994 | Dobak, III | 606/23 |
| 5,400,602 A | 3/1995 | Chang et al. | 62/50.7 |
| 5,500,012 A * | 3/1996 | Brucker et al. | 607/122 |
| 5,531,742 A | 7/1996 | Barken | 606/21 |
| 5,658,276 A | 8/1997 | Griswold | 606/24 |
| 5,800,488 A * | 9/1998 | Crockett | 607/105 |
| 5,846,235 A * | 12/1998 | Pasricha et al. | 606/23 |
| 5,876,398 A * | 3/1999 | Mulier et al. | 606/41 |
| 5,899,897 A * | 5/1999 | Rabin et al. | 606/21 |
| 5,906,612 A * | 5/1999 | Chinn | 606/21 |
| 5,910,104 A * | 6/1999 | Dobak et al. | 600/121 |
| 6,011,995 A * | 1/2000 | Guglielmi et al. | 607/99 |
| 6,095,149 A * | 8/2000 | Sharkey et al. | 128/898 |
| 6,182,666 B1 * | 2/2001 | Dobak, III | 128/898 |
| 6,319,248 B1 * | 11/2001 | Nahon | 606/22 |
| 6,383,181 B1 * | 5/2002 | Johnston et al. | 606/24 |
| 6,562,030 B1 * | 5/2003 | Abboud et al. | 606/21 |

* cited by examiner

*Primary Examiner*—Henry M Johnson, III
(74) *Attorney, Agent, or Firm*—DLA Piper US LLP

(57) ABSTRACT

Disclosed is a cryosurgical catheter which is heated in order to prevent its freezing within the lumen of an endoscope. The catheter is to be used with an endoscope to perform cryoablation on an internal tissue; e.g., the esophagus. Electric conductivity to produce heat employs an electrical conductive coating on the catheter. Also, disclosed is a fitting for use with a catheter comprising both a connection for receiving gas and an electrical connection.

27 Claims, 22 Drawing Sheets

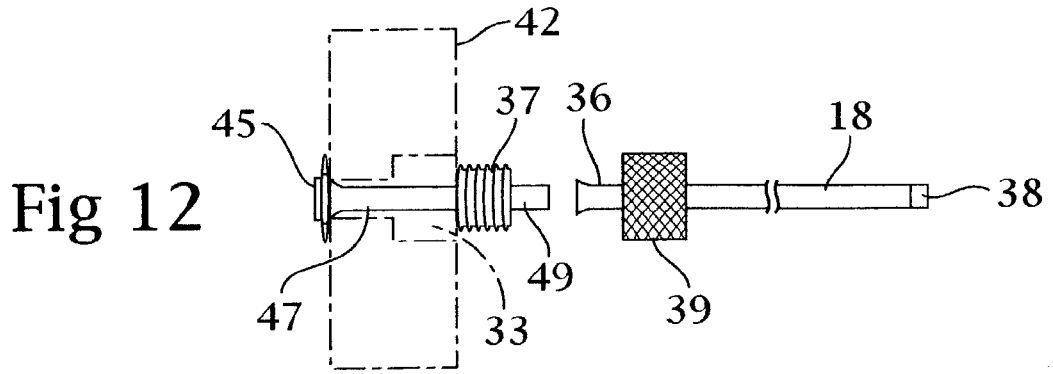
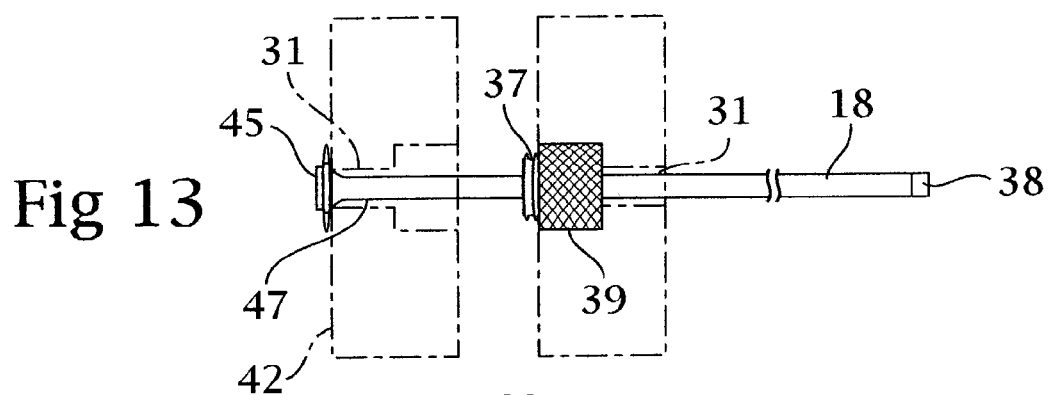
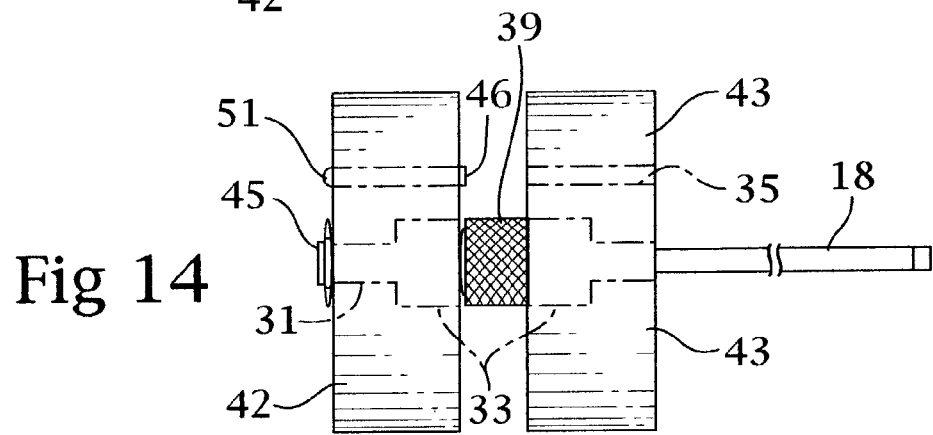
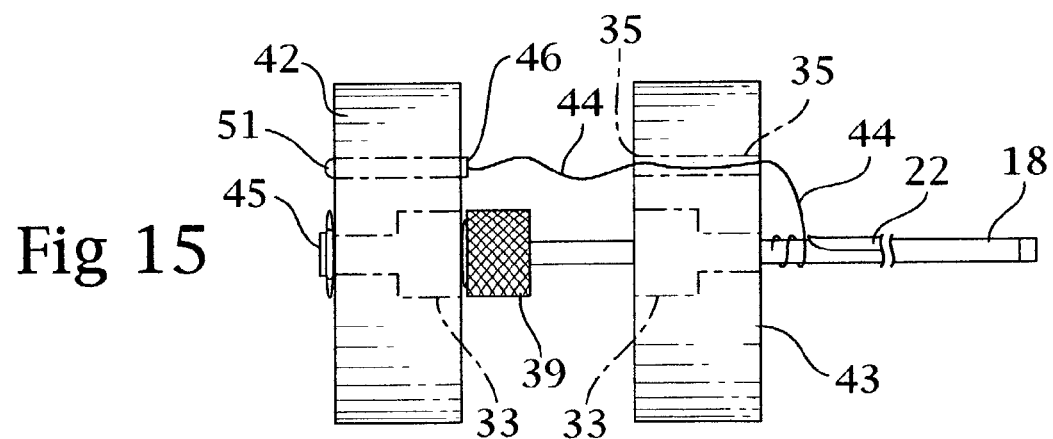

Figure 28. Cryo-catheter: electronically warmed, multi-layered, open tipped, 10F catheter.

Figure 29. Low-pressure spray cryotherapy device. A. Liquid nitrogen tank. B. Electronic console, measures mucosal temperature, time of cryo application, and duration of cryoburn. C. Cryo-catheter. D. Dual foot-pedal: controls heat to outer sheath of catheter and release of liquid nitrogen. E. Control switch to mark time of cryoburn viewed endoscopically.

Figure 31. Example of an initial cryoburn with the first prototype catheter.

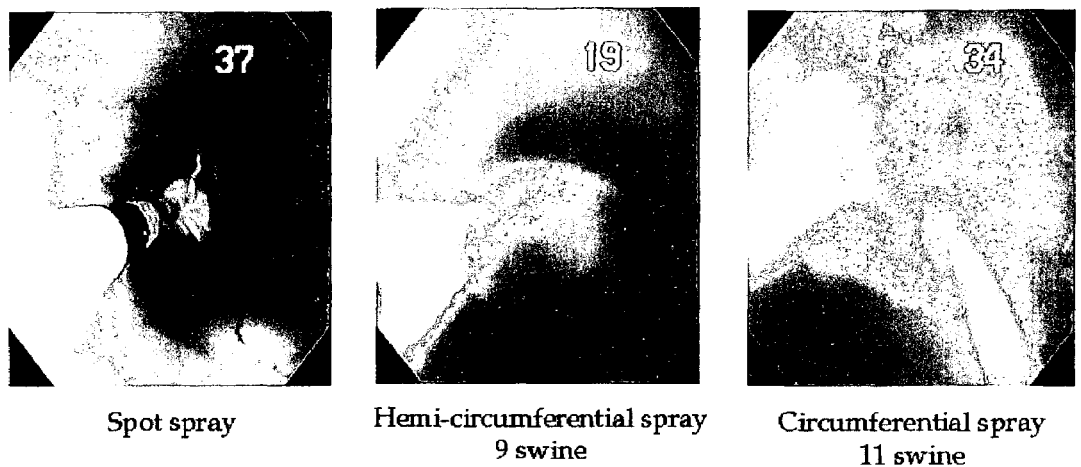
Figure 32. Phase I. Spray cryotherapy can be easily controlled via deflection of the endoscope tip to the desired target area. A cryoburn can be as small as 1-2 mm or as large as an entire circumferential segment of esophagus.

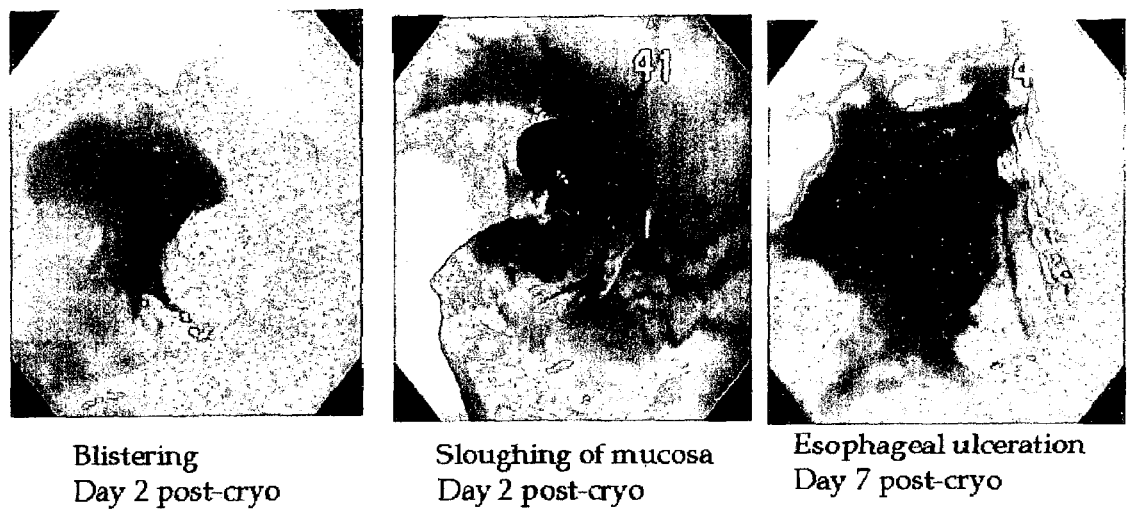
Figure 33. Follow-up endoscopy post-cryo. This particular lesion developed in association with a circumferential, 60-second cryoburn and later was associated with an esophageal stricture.

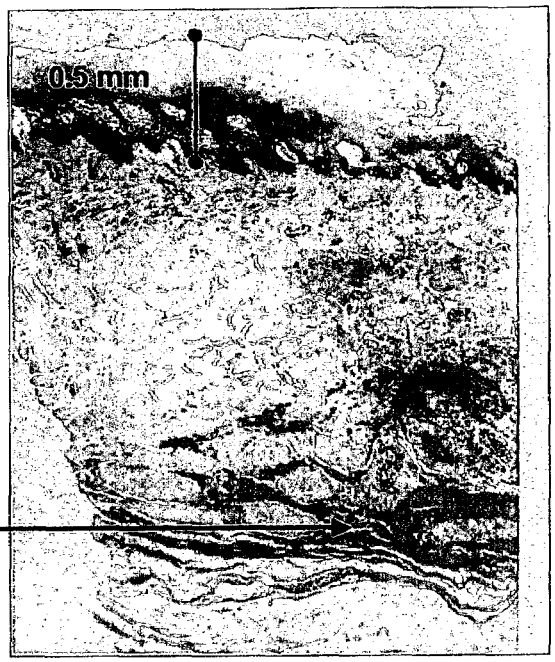
Figure 34. The epithelium remains intact immediately post-cryo. The initial injury is deeper as evidenced by submucosal hemorrhage.

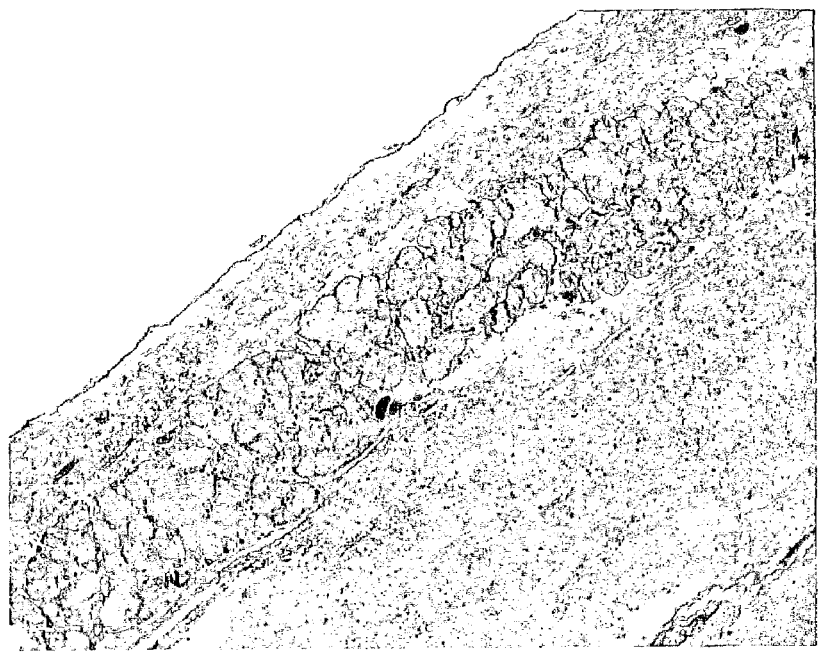
Figure 35. Esophagus 48 hours post-cryo revealing complete denudation of the squamous epithelium with slight hemorrhage into the lamina propria

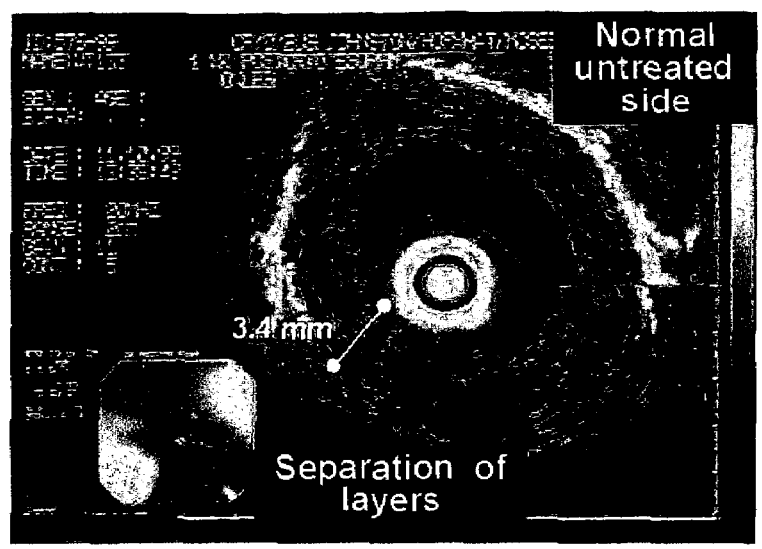
Figure 36. EUS on cryo lesion 7 days post-cryo. EUS reveals separation of esophageal wall layers.

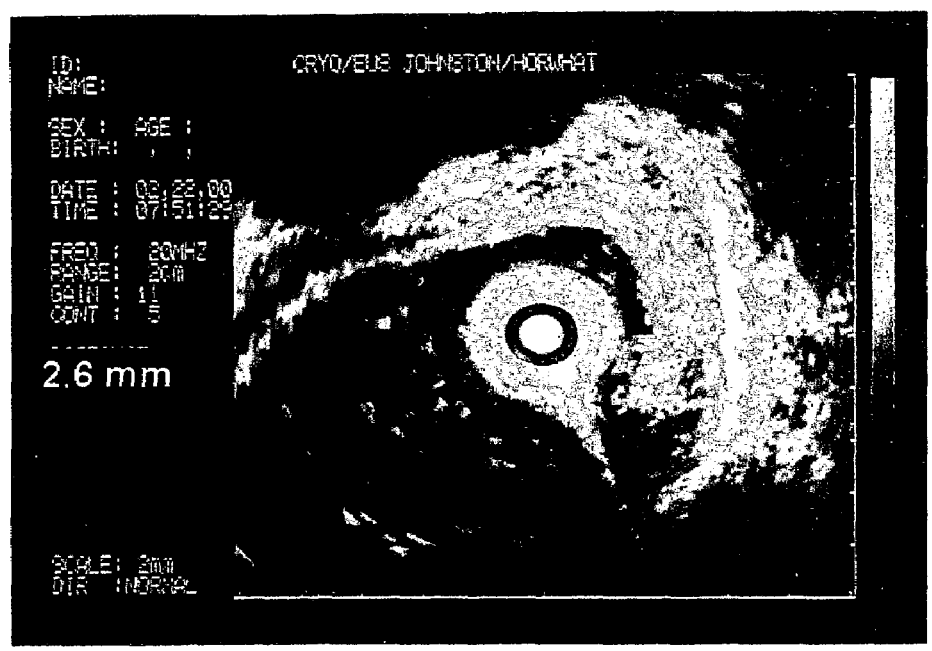
Figure 37. EUS 14 days post-cryo reveals resolution of esophageal wall edema.

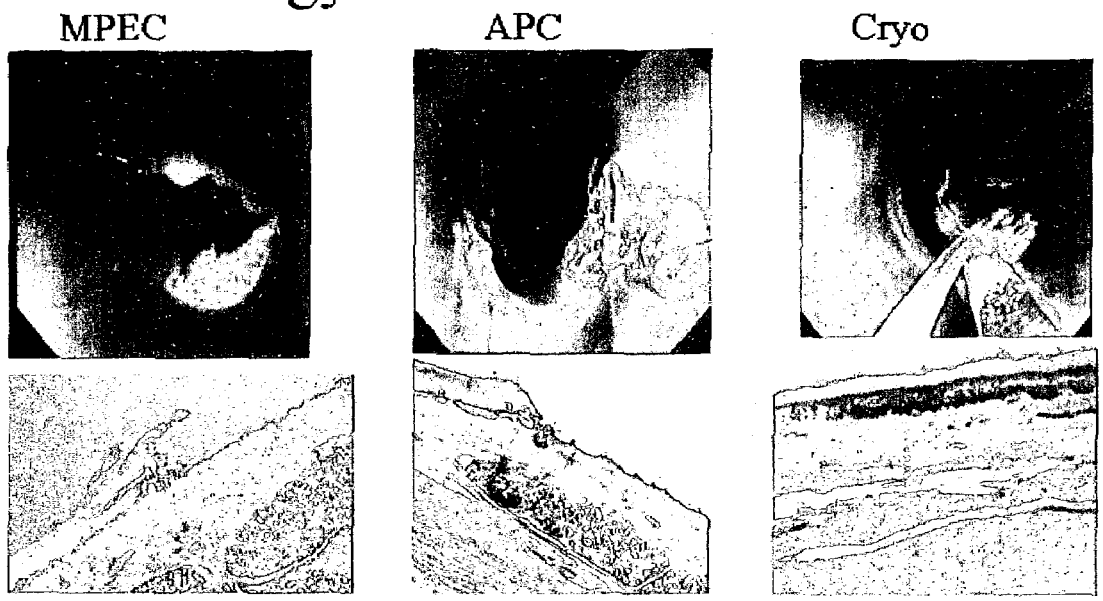
Figure 38. Comparison of MPEC, APC 60W and 90W and Cryo in swine esophagus. Histologic specimens below were taken one hour post-cryo and reveal ablated epithelium with MPEC and APC but intact epithelium with cryo.

HEATED CATHETER USED IN CRYOTHERAPY

RELATED APPLICATIONS

This application is a continuation-in-part of Ser. No. 10/106,985 filed Mar. 26, 2002, now U.S. Pat. No. 7,025,762; which is a continuation-in-part of Ser. No. 09/477,839 filed Jan. 5, 2000 now U.S. Pat. No. 6,383,181 which in turn is a continuation-in-part of Ser. No. 09/050,150 filed Mar. 30, 1998 now U.S. Pat. No. 6,027,499 which claims benefit of Provisional Application Ser. No. 60/047,484 filed May 23, 1997, the disclosures of which are herein incorporated by reference.

FIELD OF THE INVENTION

The invention finds applicability in the field of cryosurgery where a catheter is used to convey a cryogas to ablate tissue.

BACKGROUND OF THE INVENTION

In a companion application filed by the inventors, there is claimed a method for ablation of tissue in the esophagus using a cryogenic gas. In a specific therapeutic application, Barrett's esophagus is treated, although other intestinal lesions may also be treated. While the therapeutic treatment is effective, the cold cryogenic gas tends to make the catheter stiff and unmanageable, and at times rupturing the catheter. The herein disclosed invention is designed to remedy the problem of catheter stiffening. The inventors have solved this problem by a system by which the catheter is heated and its flexibility maintained during cryogenic surgery. Besides the issue of catheter flexibility, the heated catheter is intended to eliminate the freezing of the catheter to the lumen of an endoscope. Heating of the catheter will prevent ice formation which causes sticking.

Prior Art U.S. Patents

Crockett (U.S. Pat. No. 5,800,488) teaches a cryoprobe with a warming feature. The warming feature allows for the quick removal of the probe after cryosurgery. Crockett does not teach the concept of an electrically heated catheter.

Chang et al (U.S. Pat. No. 5,400,602) teaches a cryogenic transport hose designed facilitate the supply and return of cryogenic fluid such as a liquefied gas. Flexibility of the hose's maintained by using multiple layers of reflective metallized material, surrounded by a layer of foam material which, in turn, is surrounded on outer cover all covering the gas supply. An electric means for heating the transport hose is not shown by Chang et al.

Lee (U.S. Pat. No. 3,298,371) teaches a cryogenic probe useful in neurosurgery. The Lee patent also teaches an electric means for heating the exterior of the probe. This heating means is provided in the event the insulation on the exterior of the probe is inadequate to thermally isolate non-target tissue surrounding the probe. In this way, non-target areas will not be affected by the cold, and only the cold probe tip will be presented to the target area. While Lee discloses an external heating means, the reference is silent as to teaching externally heating a catheter which is to be used to convey a gas during a cryosurgical procedure.

Barken (U.S. Pat. No. 5,531,742) teaches a computer controlled cryosurgery apparatus. No electrical catheter heating means is shown by Barken.

Thomas (U.S. Pat. No. 3,507,283) discloses a cryosurgical probe whose temperature is precisely controlled to a desired heat or cold level. Thomas employs heating wire along the external surface of the instrument. Also shown is a cover of heat shrinkable polytetrafluoroethylene to protect the user's hand from the cold. This patent does not disclose the heating of a catheter which is to be used during cryosurgery in which a gas is to be applied during cryoablation.

Griswold (U.S. Pat. No. 5,658,276) teaches a heated cryosurgical probe with a heated exterior which is able to release a frozen probe from cryoablated tissue so that areas of the body not being treated by the probe are not damaged by the cold instrument. The heat is produced by a battery-energized external surface of the probe. Griswold does not teach a heated catheter used to spray a cryogas during internal cryosurgery.

BRIEF SUMMARY OF THE INVENTION

Principles of Cryotherapy

The goal of cryotherapy is to freeze a specified volume of tissue resulting in necrosis without significant damage to the surrounding "innocent" tissues. Factors that facilitate this are rapid freezing, slow thawing and repetition of the freeze-thaw cycle. The cryoburn, the lesion of cryotherapy, is recognizable as a white, sharply demarcated, frozen, patch of tissue (FIG. 31). Unlike mucosal ablation with other modalities, ablation is not immediately apparent after thawing of the cryoburn, which occurs within seconds to minutes after application of the cryogen ceases. Once the cryoburn thaws there is mucosal hyperemia. Blistering and shedding of the mucosal layer does not occur for at least 24 hours. Immediate cryonecrosis can occur at extremely cold temperatures of sufficient duration, but does not occur with spray cryotherapy as described below. Parameters that influence the degree of cryo-injury are cooling rate, tissue temperature, duration of freeze, thawing rate and repetition of the freeze-thaw cycle (Gage et al, Cryobiology 1998; Mazur, Science 1970). Mazur demonstrated that rapid freezing and slow warming lead to maximum cell death. Current investigation indicates that the necessary temperature for cell death is between $-40°$ to $-15°$ C. (10). However, to achieve immediate cell death via cryonecrosis freezing of sufficient duration at temperatures between $-76°$ C. and $-158°$ C. must be attained (Grana et al, Int. Surg. 1981).

If cell hypothermia is of sufficient duration, cell organelle and protein damage will occur leading to cell death through physical breakdown of the cell membrane or through induction of genetically controlled apoptosis. Apoptosis is a protective mechanism by which senescent, DNA-damaged, or diseased cells that could either interfere with normal function or lead to neoplastic proliferation are induced to die. Cryotherapy at relatively warm temperatures in the range of $-15°$ C. has been shown to induce cell death via induction of apoptosis (Clarke et al, Molec. Urol. 1999). This is potentially a unique mechanism for the treatment of Barrett's esophagus and dysplasia as some investigators have identified arrest of apoptosis as one of the pathologic mechanisms involved in Barrett's (Katada, Arch. Surg. 1997).

The processes associated with delayed injury begin with the immediate freeze of targeted and surrounding tissues. Consequent to this is vasoconstriction and microthrombi formation in the venules and capillaries resulting in vascular stasis. Tissue ischemia follows with subsequent cell death (Dawber et al, Prin. and Clin. Proc. 1992). This mechanism may play a unique role in gastrointestinal endoscopy in the realm of hemostasis.

The most delayed cellular mechanism associated with cryotherapy is the cryo-immune response. When neoplastic or other tissue is injured through freezing its antigens are released without being destroyed like in other thermal ablative techniques. The release of tissue antigen from cryo-injury serves as a nidus for the development of tumor specific immunity and is unique to cryotherapy relative to other thermal ablative techniques. Shulman et al demonstrated that the in situ freezing of tissue constitutes an antigenic stimulus at least equal to that obtained through the parenteral administration of antigen which is capable of generating a specific immunologic response to autologous antigens of the frozen tissue (Shulman et al, Proc. Soc. Exp. Biol. 1967). Grana et al demonstrated that in situ freezing of canine esophagus resulted in a cellular response directed to the antigens present in extracts of esophageal mucosa and muscularis and that repeated freezing resulted in an increased response to those antigens suggesting an anamnestic response (Grana et al, Int. Surg. 1981). The cryoimmune response may play a unique role in the treatment of mucosal neoplasms in the gastrointestinal tract such as adenocarcinoma of the esophagus.

Certain tissues may have variable sensitivity to cryotherapy and this difference may be exploited in treatment (Sheski, Clinics in Chest Med. 1999).

Cryosurgical Procedures

A completely automated system with sensors and a microprocessor are employed for performing cryosurgery. It is an important preferred feature of the present invention that the spray be conducted in such a manner as to allow constant visualization by the physician of the tissue treatment as it occurs. If the temperature of the lens at the distal end of the endoscope drops precipitously at the start of the liquid nitrogen spray, the moist air of the esophageal environment or of the air of the catheter which has been blown out ahead of the nitrogen flow will condense on the lens, thereby obscuring the physician's view of the operative site. This can be substantially avoided by means of the suction pump which will immediately suck out the moist air which is present prior to the arrival of the liquid nitrogen spray or cold nitrogen gas. Because of this pumping out of the moist air as the spray commences and the replacement with extremely dry nitrogen gas, substantial amounts of moisture will not form on the lens during the procedure, allowing an excellent view of the operative site by the physician during the procedure.

This condensation effect is augmented by the fact that the catheter itself is preferably not wrapped in additional insulation. This causes the temperature of the nitrogen gas exiting the catheter at the distal end to be relatively high at the beginning of the spraying operation and gradually cooling as the catheter cools. Indeed, in the tests conducted in the esophagus of pigs discussed below in the Examples, often 10-20 seconds were necessary before significant freezing was seen through the endoscope. If the catheter is substantially insulated, the interior of the catheter will cool much more quickly as it will not be picking up heat from the outside. With this insulated catheter, it is to be expected that the liquid nitrogen would be sprayed onto the tissue almost immediately, causing much faster freezing and, thus, allowing less control on the part of the physician.

Another reason that the lens does not fog or frost in the present invention is that the esophagus is flushed out with nitrogen gas, which is extremely dry. The nitrogen gas is moisture free because the liquid nitrogen is condensed out of atmospheric gases at a temperature $-196°$ C. colder than the temperature at which moisture is condensed out.

The combination of relatively warm, and completely dry nitrogen gas, together with suction flushes all moist air from the esophagus. As the temperature of the gas entering the esophagus falls, so does the surface temperature of the camera lens. Ordinarily at that time the lens would be cold enough to condense moisture and fog, however, since the esophagus is dried out (in contrast to its usual highly moist state) there is no moisture to condense. Thus, the lens stays un-fogged and un-frosted and continues to provide a clear view of the operation. On the other hand, if the esophagus is not vented with suction and/or the esophagus is not preliminarily flushed with dry nitrogen gas (perhaps because the catheter is insulated, lowering its heat capacity, and/or the nitrogen delivery pressure is too high), then the lens is likely to fog or frost and the physician cannot operate effectively.

In order to deal with the moist air problem, there is supplied in the preferred embodiment of this invention a nasogastric tube. During the cryosurgical procedure the nasogastric tube is inserted prior to inserting the endoscope. The nasogastric tube, when connected to a pump, can serve to evacuate moist air from the esophagus prior to cryosurgery. With moist air removed, the TV camera lens is not obscured by fog and the physician can perform cryosurgery with an unobstructed view. Alternatively, if fogging occurs during cryosurgery, the nasogastric tube and pump can be used to evacuate the esophagus.

In the most preferred embodiment, the composition of the catheter or the degree of insulating capacity thereof will be selected so as to allow the freezing of the mucosal tissue to be slow enough to allow the physician to observe the degree of freezing and to stop the spray as soon as the surface achieves the desired whiteness of color (cryoburn). The clear observation results from the removal of the moist air and sprayed nitrogen by the vacuum pump; in combination with the period of flushing with relatively warm nitrogen prior to application of the spray of liquid nitrogen which is caused by the relative lack of insulation of the catheter. Preferably, the catheter has a degree of insulation which permits at least five seconds to pass from the time said means for controlling is opened to the time that liquified gas is sprayed onto the mucosa. As a preferred embodiment, an electrically heated catheter is described herein.

An electronic monitoring and recording system is to be used during cryosurgery. The electronic components of the system comprise a temperature sensor or probe and timer. Also connected to the monitoring and recording system are the foot-pedal for actuating the solenoid and recording console. An electric power cord runs from solenoid to control box.

The temperature sensor is thin and can be inserted into the esophagus beside the catheter. In a preferred embodiment, the temperature sensor and catheter can be inserted separately or as an integral unit of sensor and catheter combined, or alternatively the sensor can be inserted through an extra lumen of the endoscope to come in contact with the tissue of the esophagus. The temperature sensor sends temperature readings to the electronic monitoring and recording system for processing and recordation.

The liquid gas flow is started by actuating solenoid foot-pedal and ends with release of the solenoid foot pedal. The electronic monitoring and recording system records the times at which cryoburn starts and ends. Temperature in the context of time will be recorded for the cryosurgery. This recordation allows for better data acquisition and documentation.

There is an automatic cut-off if a time or temperature limitation is exceeded. In the event of a cut-off, the electronic monitoring and recording system can be reactivated by pushing the reset button. Current time and temperature readings are presented in the windows as LED numbers. The windows in the system will indicate total time; shut-down time; cryotime; cryotime set; and temperature. Within the main console of the electronic monitoring and recording system is a printing unit which prints and records the time and temperature during the cryoburn. Every event is recorded, e.g. time, on and off, temperature, etc.

The electronic console can be preprogrammed to be patient specific.

Kit Supplying Components of the Invention

The components or paraphernalia required to practice the method of the present invention may be packaged and sold or otherwise provided to health-care providers in the form of a kit. The kit is preferably sealed in a sterile manner for opening at the site of the procedure. The kit will include the catheter, having the spray means at one end, as well as a means for connecting the catheter to the source of liquified gas. This means for connecting may be a simple luer connection on the opposite end of the catheter from the spray means. However, the term "means for connecting said catheter to a source of liquified gas" is intended to include any other device or apparatus which allows the catheter to be connected to the gas source.

Many of the components of the cryosurgical system are conventional medical appliances. For example, the endoscope is a conventional medical appliance and would not necessarily have to be supplied as part of a kit. One of the components to be supplied in a kit or sterilized package is a combined catheter-bleeder vent. Also, the heated catheter assembly would be supplied in a kit or sterilized package.

The inventors envision supplying the heated catheter and vent unit as a separate item. In this way, the unit can be supplied in a sterile packet or kit to be used with existing equipment found in hospital operating rooms. The kit may contain a nasogastric tube, or the kit could contain only a heated catheter unit.

The means for controlling the flow of liquified gas to the catheter is also preferably present in the kit and may be connected to or may be part of the means for connecting the catheter to the source of liquified gas. For example, the connector may contain a valve therein or the valve may be a separate element connected between the connector and the catheter or between the connector and the nitrogen source. The connector besides being connected to the source of gas can also be a connector to the source of electricity.

The kit will also optionally contain the means for withdrawing gas, such as a tube and a means connectable to the tube for withdrawing gas from the tube. Such means connectable to the tube for withdrawing gas may be a vacuum pump or any other device or apparatus which will accomplish the function of withdrawing gas from the tube. The vacuum pump is optionally omitted from the kit as a source of vacuum is often found in hospital rooms in which such a procedure is to take place.

The means for blocking the lumen is also optionally present within the kit. Thus, for example, the kit may contain a balloon catheter or any other device or apparatus which can accomplish the function of blocking the lumen when in use.

The term "container" or "package" when used with respect to the kit is intended to include a container in which the components of the kit are intended to be transported together in commerce. It is not intended to comprehend an entire procedure room in which the individual components may happen to be present, an entire vehicle, a laboratory cabinet, etc.

Pressure During Cryosurgery

In an embodiment of the invention, the bleeder valve has been found to be unnecessary so long as low pressure can be maintained by other means. In the improved embodiment, a cryoburn is carried out without the need for a bleeder valve. In this new embodiment with the tank pressure at 45 psi and the catheter being a 9 french, the cryo-procedure took 4 minutes and 50 seconds. With a 10 french catheter using 45 psi, the cryo-procedure took 2 minutes and 50 seconds to achieve a cryoburn temperature. With the bleeder valve, it takes 10-20 seconds to achieve cryoburn. The ideal low pressures operative for this invention should be in the range of 3-45 psi. The most ideal pressure is determinable by those skilled in the art.

Regarding pressure 40 psi is preferred, the cryogenic spray will function at higher pressures. The system could be made to work at tank pressures as high as 300-400 psi by adjusting the size of the bleeder line and by using a larger size catheter. Note, however, that tip pressure is only one factor to be considered for producing cryoburn. Other factors to consider are size of catheter and length of time of application. Certain clinical conditions may require differing pressures and differing time of cryoburn. The nozzle or tip pressure for cryosurgery should not be so high as to puncture any internal organ and optimum nozzle pressure can be determined by those skilled in the art.

The cryosystem could function at significantly higher nozzle pressures by adjusting other factors of the protocol. Significantly higher nozzle pressures would be operative if the treatment exposed the tissue to shorter cryoburn exposure time. The higher pressures may necessitate the need for a vacuum line to remove the excess volume of nitrogen introduced into the body cavity.

In the future, technology may reduce the size of the components of the endoscopic. This would allow additional diameter for the catheter. If the diameter of the catheter is increased, the flow of the cryogen could also be increased without affecting the treatment parameters. Potentially, the catheter could be used along side of the endoscope rather than through the lumens of the endoscope. Then the size limitation of the catheter could be modified.

Additionally, the holding tank could be stored at much greater pressures. The higher the storage tank pressure, the less nitrogen bleed off that will occur, resulting in a lower loss of nitrogen during storage. The temperature of the liquid nitrogen stored at pressures higher than 22 psi is warmer than that of the liquid nitrogen stored at 22 psi. At 200 psi (this is the highest pressure tested) the liquid nitrogen is still cold enough to deliver a cryoburn.

The high-pressure tank can be staged in any conceivable manner. A 700 psi storage tank could be staged down by altering the size of the bleeder, by altering the size of the catheter, or by adding additional bleeder lines. A 700 psi flow to 3-5 psi can be accomplished in a number of ways as understood by those skilled in the art.

The inventors have checked nozzle pressures of catheters and found for tank pressure of 22 psi and a 9-French catheter the nozzle pressure is 2-3½ psi; and for tank pressure of 22 psi and a 10-French catheter the nozzle pressure is 3.2-5.9 psi.

It is clear from experiments performed that a bleeder valve is not absolutely essential to this invention since low pressure cryoablation can be carried out through low head pressure in the storage tank or through selection of the proper inner diameter of the catheter. Based on experiments carried out with the bleeder valve embodiment a shorter time period is required for cryoburn.

A convenient and preferred means of supplying the cryogenic gas under pressure and in liquid form would be to employ a compressor to compress the gas to be used with the catheter before it is to be used in cryosurgery.

Cryoburn Conditions

The inventors have concluded from preliminary test results that a 30 second "cryoburn" time was adequate to ensure the appropriate tissue destruction, and thus appropriate cellular healing of damaged tissue (this conclusion was based on a 30 day follow up period). "Cryoburn" is a term defined by the instance that the normally "pinkish" esophageal tissue turns white (much like freezer burn). A range for the "cryoburn" time could be 5-10 seconds to 2 minutes or more depending on the substrate to be treated.

Due to the nature of the system, "cryoburn" does not immediately occur, but rather requires that the entire fitting and catheter system become cool. Typically this required approximately 20-30 seconds from the time that the solenoid foot pedal is depressed, and liquid nitrogen is allowed to flow from the tank.

During animal testing the approximate temperature that cryoburn was first observed was at approximately −10 degrees C. The temperature range for cryoburn would be approximately −10 to −90 degrees C.

In carrying out the procedure, a nasogastric tube is first inserted into the esophagus, after which an endoscope is inserted. Optionally, attached to the endoscope will be a temperature probe to sense the temperature and report the temperature to the recording console. Once the nasogastric tube, endoscope and temperature probe are in place, the catheter attached to the gas supply will be inserted into a lumen of the endoscope. Before liquid gas is supplied, the esophagus is ventilated using the nasogastric tube to remove moist air from the esophagus (if required). With the moisture evacuated and the endoscope properly positioned, gas can be supplied to the catheter by actuating the solenoid with foot pedal. Once the solenoid is actuate gaseous nitrogen and then a spray of liquid nitrogen will come from the tip of the catheter. The cryoburn will generally last for 30 seconds to two (2) minutes.

In further developing the cryogenic spray system, the inventors envision positive advantages in over-exposing the esophagus to the cryoburn. The scarring that occurs could be helpful for patients that have chronic reflux. There are currently a number of techniques that work to "tighten" the lower esophageal sphincter. The scarring that occurs during over exposure in the cryosurgical method of the disclosed invention could be an additional treatment of chronic reflux.

Experiments

The cryospray was used in experiments to assess the efficacy and safety of this device in mucosal ablation in the distal esophagus of swine. The catheter was a long 7Fr ERCP-like catheter placed through the biopsy channel of an Olympus GIF-100 endoscope. The swine were sedated using telazol and xylazine given intravenously. General anesthesia was not necessary. Liquid nitrogen was sprayed on the distal 2 cm of the esophagus in 16 swine under direct endoscopic observation until a white "cryo-burn" appeared, usually within 10-20 seconds. Duration and location of the spray were varied to assess histologic response and depth of "cryo-burn". The swine were then re-endoscoped on days 2, 7, 14, 21 and 30 to obtain biopsies from the injury site, assess mucosal ablation and re-epithelialization. All swine were then euthanized and underwent necropsy.

Freezing of the esophageal mucosa was recognizable by a white "cryo-burn" with sharply demarcated margins. This was followed by slow thawing within minutes and then mucosal erythema. Sixteen swine underwent hemi-circumferential to circumferential cryotherapy of their distal esophagus varying the duration of "cryo-burn" from 10-60 seconds. Blistering and sloughing of the superficial mucosa occurred within 2 to 7 days of the cryospray. Mucosal damage occurred only at the cryo site. Biopsies 48 hours after cryospray consistently demonstrated coagulative necrosis involving the mucosal layer and biopsies 30 days after cryospray consistently demonstrated complete re-epithelialization of the injured area.

These experiments on living swine, which are a valid model of the human esophagus, establish that cryotherapy spray of liquid nitrogen via upper endoscopy is a simple technique capable of inducing controlled superficial mucosal damage with complete healing in the esophagus.

The low-pressure device (FIGS. 28 and 29) described by Johnston (Gastrointest. Endoscop. 1999) and colleagues, uses liquid nitrogen in a specially designed system that operates at a maximum of 30 psi. The catheter, 10F, is multilayered. Its outer sheath is coated with a special polymer that can be warmed during the cryo application, thus maintaining catheter pliability and the unique ability to operate at a very low pressure. This device also uses a foot pedal for control of gas release and a temperature probe for monitoring mucosal temperature during the cryo application. With this delivery system, the depth of injury is controlled by manipulating 3 parameters: the duration of cryo application, extent of cryoburn viewed endoscopically, and the temperature of mucosa at the time of application. These parameters are monitored via a special software program and device that is part of the cryogenic system (FIG. 29).

Low Pressure Cryo-Therapy Device

Four separate phases of animal research have been conducted with the low-pressure device. In the first phase, twenty swine underwent cryoablation of the distal 2-3 cm of their esophagus with liquid nitrogen in either a hemi-circumferential or circumferential pattern and were followed for one month post-cryotherapy (Johnston, Gastrointest. Endosc. 1999). In the second phase, 8 swine were treated hemi-circumferentially to the distal 3 cm of the esophagus and followed for 90 days. In the third phase of experiments, 4 swine underwent endoscopic ultrasound (EUS) of their esophagus pre-cryo, immediately post cryo and then at 48 hours, 7 days and 14 days to assess the effects on the esophageal wall. In the final phase, one swine was treated in different locations with Argon plasma coagulation (APC), Multi-polar electrocoagulation (MPEC) and cryotherapy. The lesions were then compared both endoscopically and microscopically.

Phase I

In twenty swine liquid nitrogen was sprayed hemi-circumferentially or circumferentially to the distal 2-3 cm of the esophagus. Duration of spray was varied from 10 to 60 seconds. The cryoburn appeared at mucosal temperatures between 0 to −10° C. and was limited to the targeted site. Mucosal ablation was noted 2 to 7 days post cryo in 19 of the 20 swine. The swine esophagi were completely normal at 30 days in 17 of the 20 animals. Three developed esophageal strictures and one, aspiration pneumonia. All strictures occurred in the circumferentially treated group. The aspiration pneumonia occurred in the first swine ever treated and occurred secondary to gastric insufflation with air. Two of the three strictures were minimal with easy passage of the scope; the third would have required dilation. Complete mucosal healing was observed in all swine by week 4. There were no deaths attributable to cryotherapy. This initial study demonstrated feasibility, efficacy and safety in mucosal ablation relative to other mucosal ablative techniques (see FIGS. 32 and 33).

Phase II

In this phase hemi-circumferential cryoablation of the distal 3 cm of the esophagus was performed in 8 swine using a 45 second treatment cycle. Complete ablation was noted at the targeted area in all swine at 48 hours. Residual ulceration persisted in all up to 7 days post-cryo followed by complete healing with no stricturing by 4 weeks follow-up. There were no complications and the swine were followed for a total of 90 days with no development of esophageal stricturing or complications. They gained weight normally.

Phase III

Four swine underwent EUS of their distal esophagus to assess wall thickness and establish baseline anatomy. Following baseline EUS, each swine underwent a 45 second hemi-circumferential cryoburn to the distal esophagus which was followed by repeat EUS immediately and then at 2, 7 and 14 days (FIGS. 36 and 37). The cryoburn became endoscopically evident at −9° C. The coldest mucosal temperature measured was −66° C. occurring at the end of the 45-second treatment. After EUS at 14 days, the swine were euthanized and underwent esophagectomy to assess the esophagus histologically. EUS demonstrated edema of the mucosa and submucosa 5 minutes post cryo. At one week there was separation of the mucosal layer from the underlying structures. Associated with this was edema throughout the other layers of the esophagus at the cryo site. In most instances the wall thickness doubled. These findings resolved by day 14 post cryo. Full thickness biopsies were obtained on one of the swine to evaluate cryo lesions at two different stages of evolution, one less than an hour old (FIG. 34) and one approximately 48 hours old. These biopsies revealed extravasation of RBCs into the submucosa with normal overlying epithelium at one hour, while another site 48 hours post cryo (FIG. 35) revealed complete ablation of the epithelial layer (0.5 to 1.0 mm) with mild transmural inflammation.

Phase IV

In this phase one swine had three different ablative modalities applied to the esophagus. In the very distal esophagus a cryoburn was applied in a 1-2 cm hemi-circumferential pattern for 45 seconds. The coldest mucosal temperature measured at the end of the freeze cycle was −25° C. Proximal to this, MPEC was applied at 24 Watts via 10F Gold probe (Microvasive, Watertown, Mass., USA) to a 1-2 cm area. Proximal to this, APC was applied at 90 Watts on one side of the esophagus and at 60 Watts on the opposing side using a flow rate of 2 L/min (ERBE USA, Inc., Marietta, Ga.). The swine was then re-endoscoped 48 hours latter and repeat ablation with all three modalities was performed in different areas followed by euthanasia and esophagectomy to assess both the acute and 48 hour lesions. See FIG. 38. Epithelial ablation was immediate for both APC and MPEC whereas the epithelium remained intact at the cryo site one hour post-ablation. At 48 hours post-ablation there was an extensive inflammatory response extending into the esophageal wall for APC and MPEC. It was transmural for APC at 90 W and less extensive for APC at 60 W. The MPEC inflammatory response was similar to the APC at 60 W response. The cryo inflammatory response was significantly less than APC or MPEC.

Depth of Injury in Cryotherapy

Barrett's esophagus is a mucosal disease defined as the presence of specialized intestinal metaplasia in the esophagus. This includes not only the epithelial elements but also the glandular structures down to the level of the muscularis mucosa. Barrett's epithelium is on average 0.5 mm thick with Barrett's mucosa 1.5 mm thick (Ackroyd, J. Clin. Path. 1999). The esophageal wall is thickest distally measuring approximately 4 mm by EUS (Faigel, Gastrointest. Endosc. 2002). Depth of injury reported in the literature varies considerably for each ablative modality. The depth for MPEC is between 1.7 to 4.8 mm depending on watt setting, degree of pressure applied to the probe and duration of application (Sampliner, Gastroenterology Clinics North America 1997). PDT is reported to have a depth of 1-2 mm but seems inconsistent with the high stricture rate that exceeds that of MPEC or APC. Sampliner reports that depth of injury generally follows this pattern: PDT and Nd:Yag>MPEC>Argon laser (Sampliner, Gastroenterology Clinics North America 1997). In our study (APC, MPEC and cryo) comparing depth of injury side by side in the same living animal we learned the following. Full depth of injury is not readily apparent upon completion of an ablative treatment and evolves over time depending on the technique used. There are both immediate and delayed injuries contributing to the final depth of ablation. For APC and MPEC, there is immediate ablation through cautery of the tissue contacted by the argon gas or MPEC probe accounting for the immediate destruction of the epithelial layer noted in FIG. 38. For APC, MPEC and cryo there is also a delayed inflammatory response, which results in cellular necrosis and extends the depth of injury depending on the degree of inflammation. For cryo, depending on the maximum negative temperature achieved (at least −20° C.) there is immediate ablation of epithelium caused by cryonecrosis, not observed in this particular comparative treatment protocol. There is also delayed injury resulting in ablation that occurs as a result of the processes described above (Gage, Cryobiology 1998). Epithelial ablation (0.5-1.0 mm) occurred immediately for APC and MPEC and was easily detected on full thickness biopsy one hour after application. In the cryotherapy lesion the epithelium remained intact at one hour. However, significant ablation did occur over time through the subsequent inflammatory and delayed responses described in the principles of cryotherapy section of this chapter. When compared side by side, the inflammatory response was greatest with APC at 90 W followed by APC at 60 W then MPEC and then cryo. Microscopically, depth of injury ranged from 4-1 mm and paralleled that of the inflammatory response in the same order. From phase one of the cryo studies, assessed via endoscopy, gross injury was delayed and peaked between 2 to 7 days post cryo. However, by four weeks healing was complete in all swine. Depth of ablation based on these studies is approximately 1-2 mm and is very similar to MPEC.

Heated Catheter Embodiments

BRIEF DESCRIPTION OF THE DRAWINGS

FIGS. 12-18 show the method for assembling the hub portion of the heated catheter.

FIG. 24 is a plan view of the gas and electric connection joined to the hub. The arrows show the direction for joining the components.

FIGS. 25 and 26 are cross-sectional views taken off of 25-25 and 26-26 of FIG. 20.

FIG. 27 is an enlarged longitudinal cross-section of the heated catheter.

FIGS. 31 through 38 are photographs of cryoburns and histology resulting therefrom.

DESCRIPTION OF THE INVENTION

Figure 1:
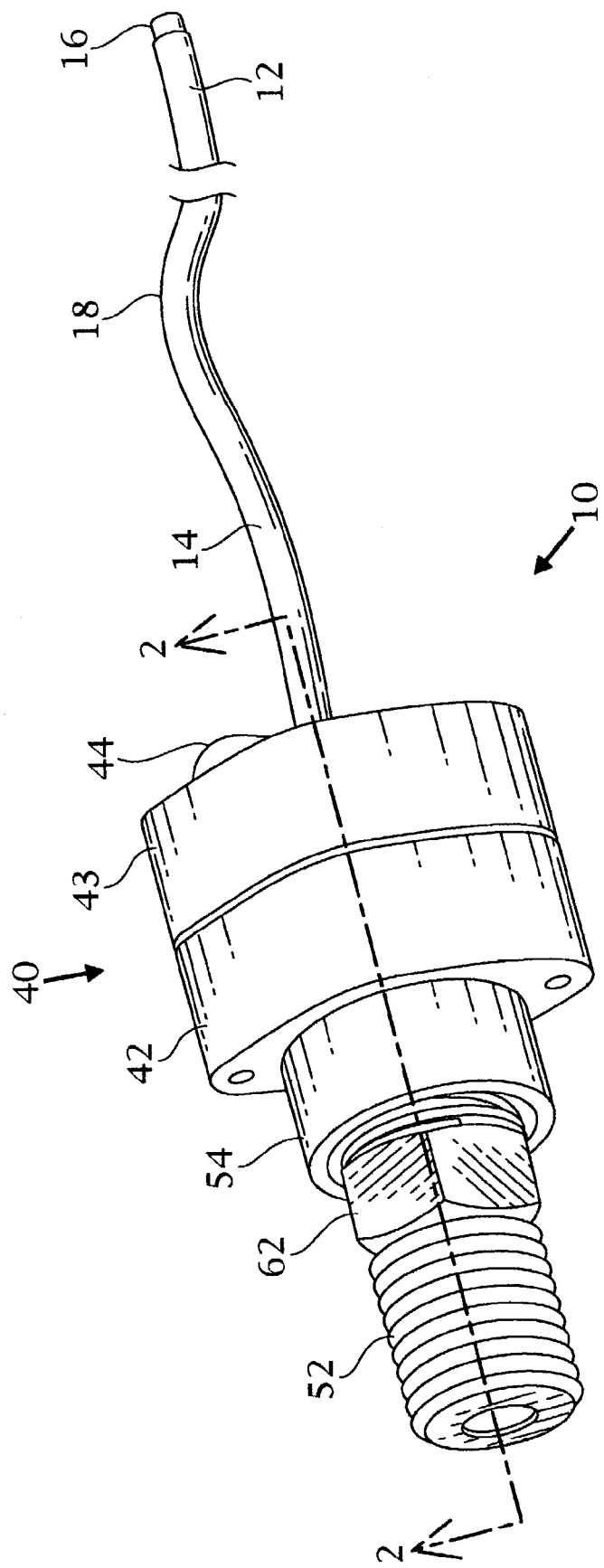
FIG. 1 is a perspective view of the heated catheter assembly. Part of the catheter is broken away for ease of illustration.
Figure 2:
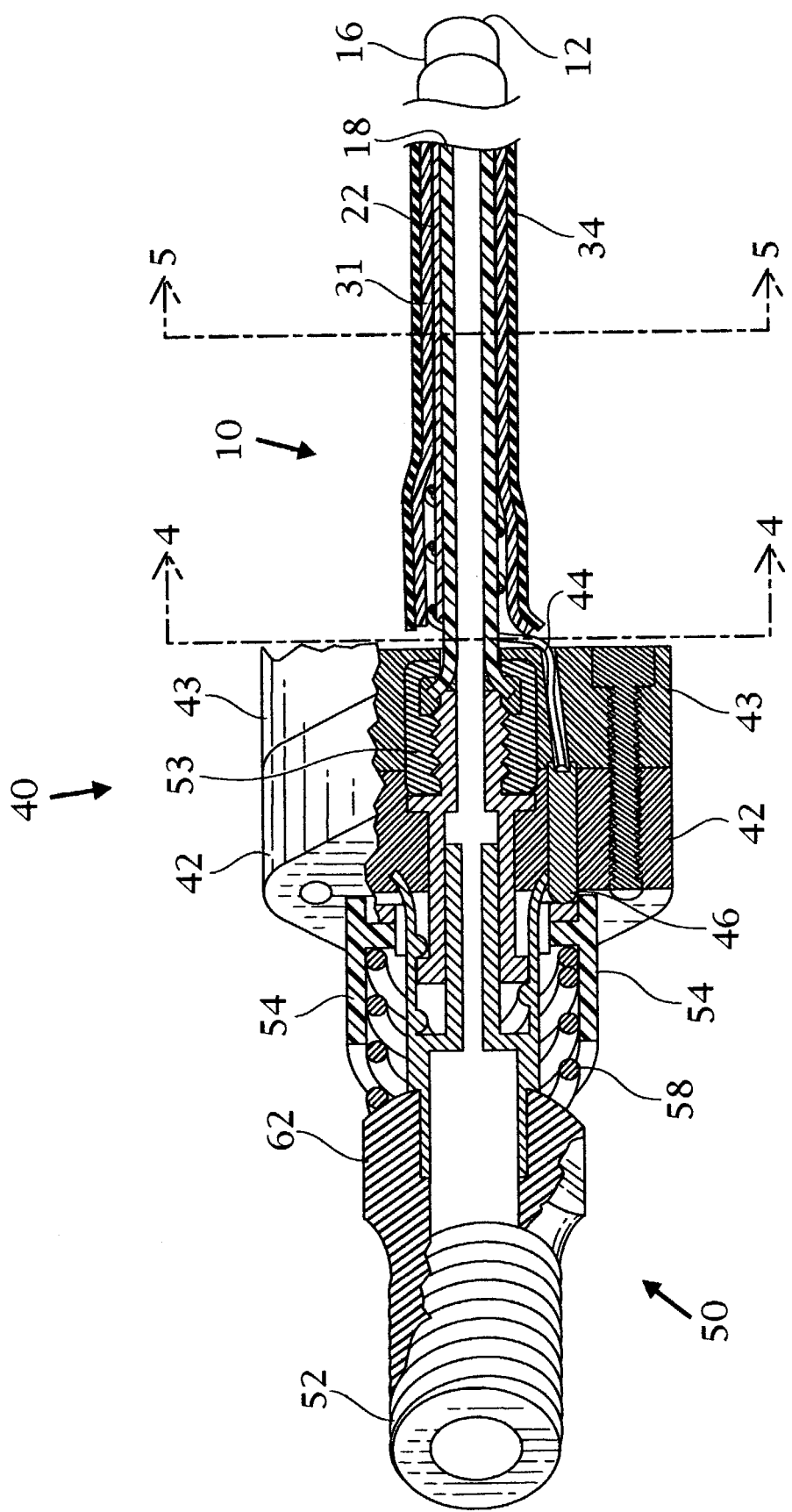
FIG. 2 is a cross-section of the heated catheter assembly, taken along 2-2 of FIG. 1, with the hub portion broken away.

With reference to FIGS. 1 and 2, a heated catheter assembly 10 has a catheter 18 with a distal end 12 and a proximal end 14. As part of the catheter assembly 10 there are a hub 40 having a top portion 42 and a base 43. The top portion 42 of the hub 40 has a gas and electric connector subassembly 50 for attaching the gas line and two contact points for making electric contact with the luer lock and threaded gas nipple 52 (described more fully in FIGS. 19-27).

Figure 3:
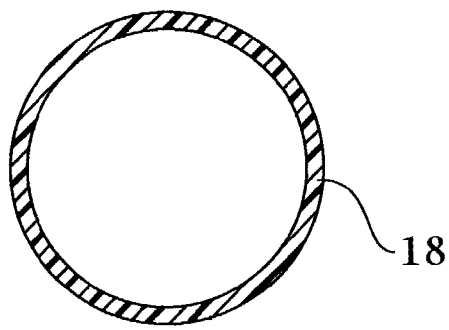
FIGS. 3, 5 and 6 are views taken along cross-section 5-5 of FIG. 2 to show components forming the heated catheter.
Figure 4:
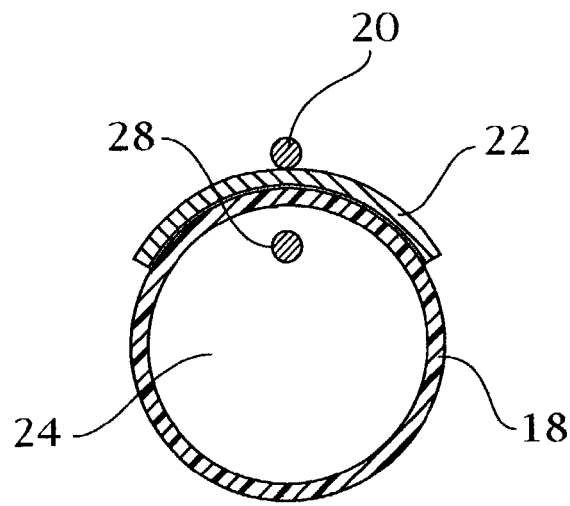
FIG. 4 is a cross-section taken along 4-4 of FIG. 2.
Figure 5:
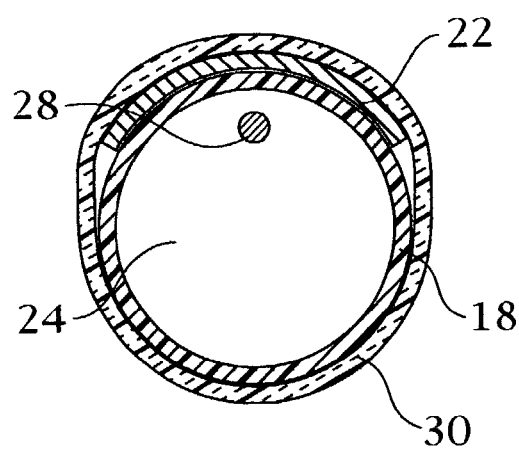
Figure 6:
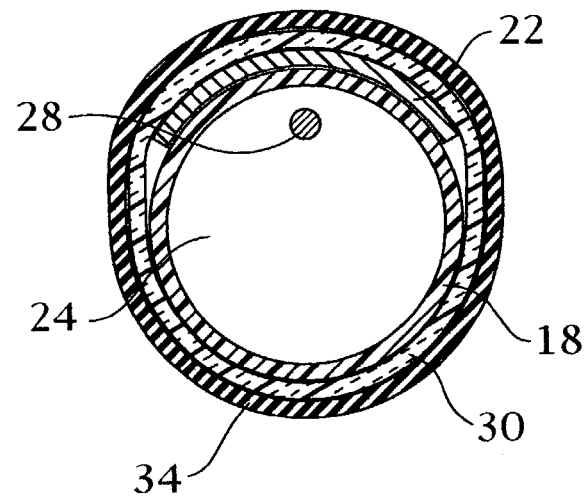

Referring to FIGS. 3-6, the order for constructing the heated catheter is shown in cross-section. Catheter 18 is shown in FIG. 3. FIG. 4 describes the catheter 18, with internal copper wire 28, the external copper wire 20 outside of the catheter and copper foil 22. Copper wire 20 being attached to copper foil 22. Wire 28 runs the length of the internal portion of the catheter 18 and exits at the distal end where it is held in place by a hypodermic tube or stainless sleeve 38 (see FIG. 9). The stainless sleeve 38 presses over the wire 28 exiting the distal end of the catheter 18 to sandwich the wire between the catheter 18 and stainless sleeve 38. With reference to FIG. 5, an electrodag coating 30 covers part of the catheter, that is, the electrodag covers a portion of the catheter contacting a portion of the conductive foil (as explained more fully below). The electrodag coating is a conductive coating and is an integral part of the heated catheter. Finally in FIG. 6 a parylene (dielective insulator coating) coating 34 covers the electrodag coating 30.

Figure 7:
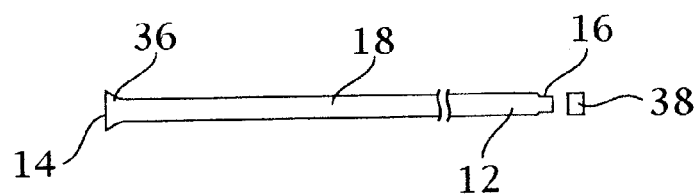
FIGS. 7-11 illustrate the steps taken to construct the heated portion of the catheter. These views are cross-sections taken longitudinally as 2-2 in FIG. 1.

With reference to FIG. 7 catheter 18 has a flared end 36 and stainless sleeve 38. The flared end 36 of the catheter allows for a better seal between the proximal end of the catheter and gas supply channel as more fully explained in FIGS. 12-15 and 27.

Figure 8:
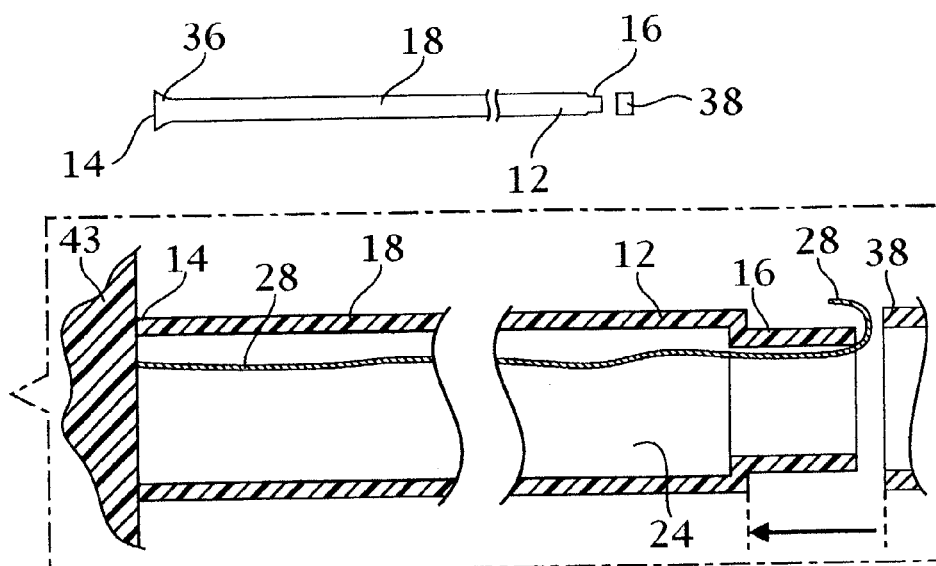
Figure 9:
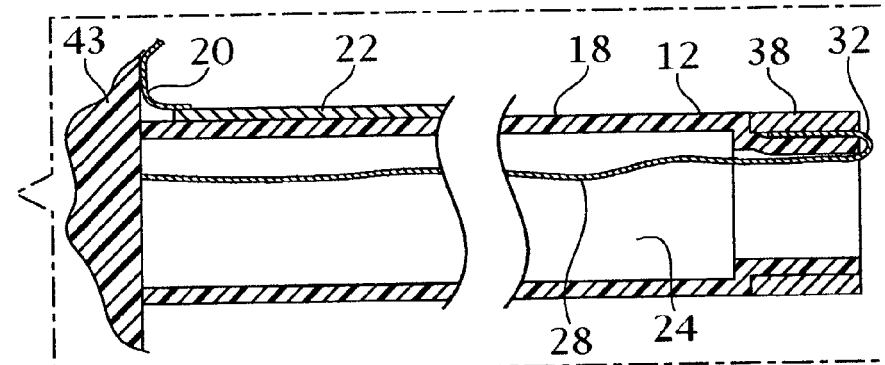
Figure 10:
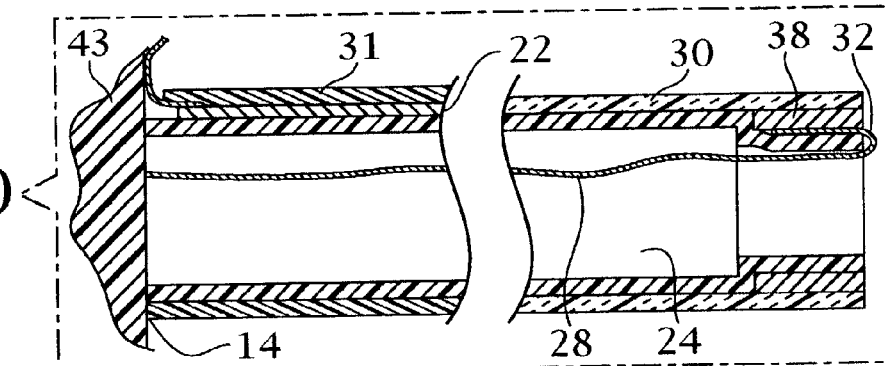
Figure 11:
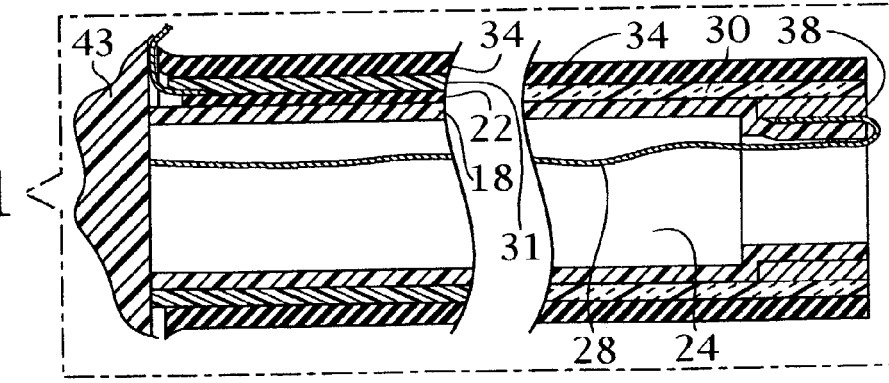
Figure 27:
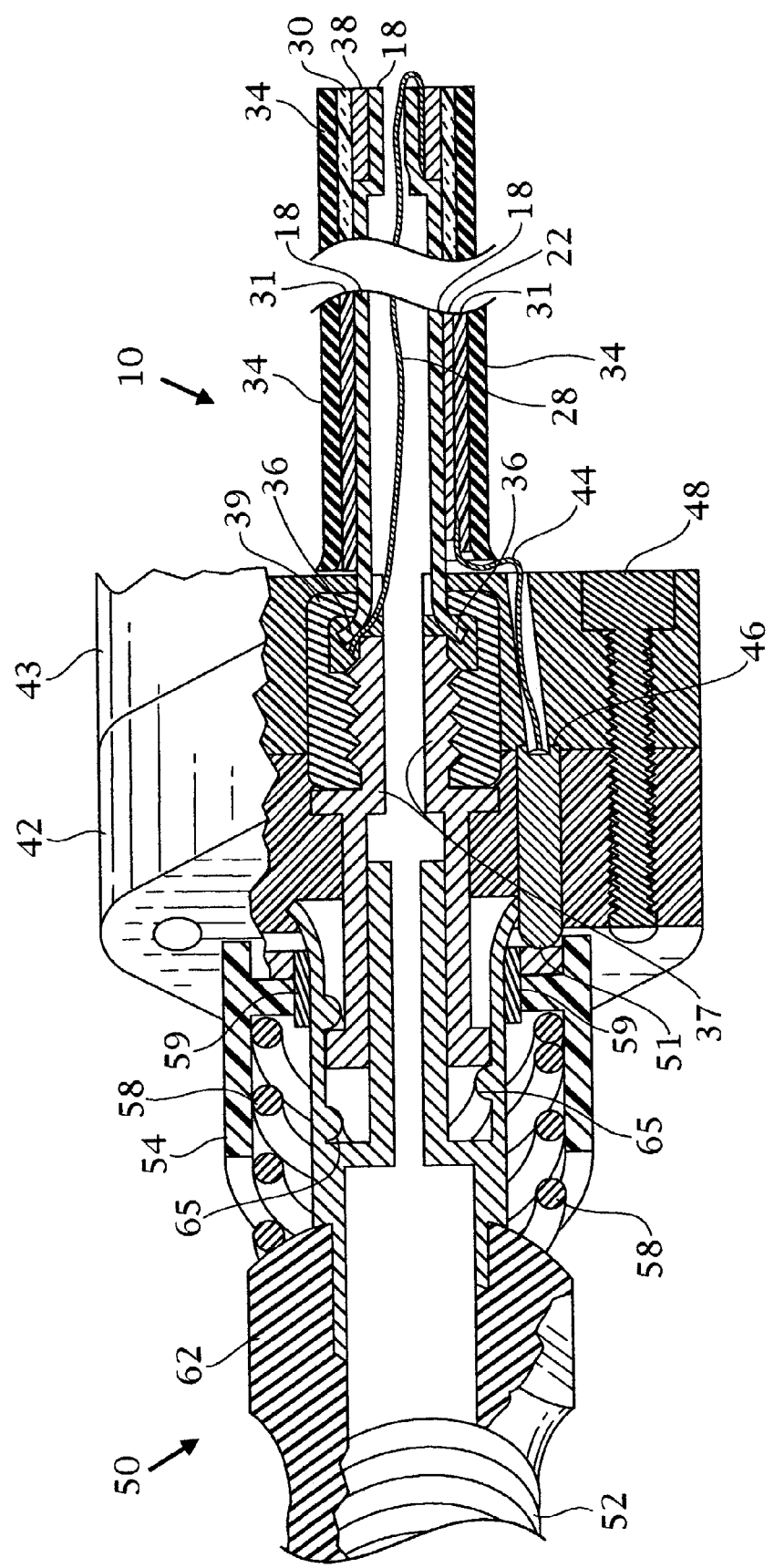
Figure 28:
FIG. 28 is a photograph of the heated catheter.
Figure 29:
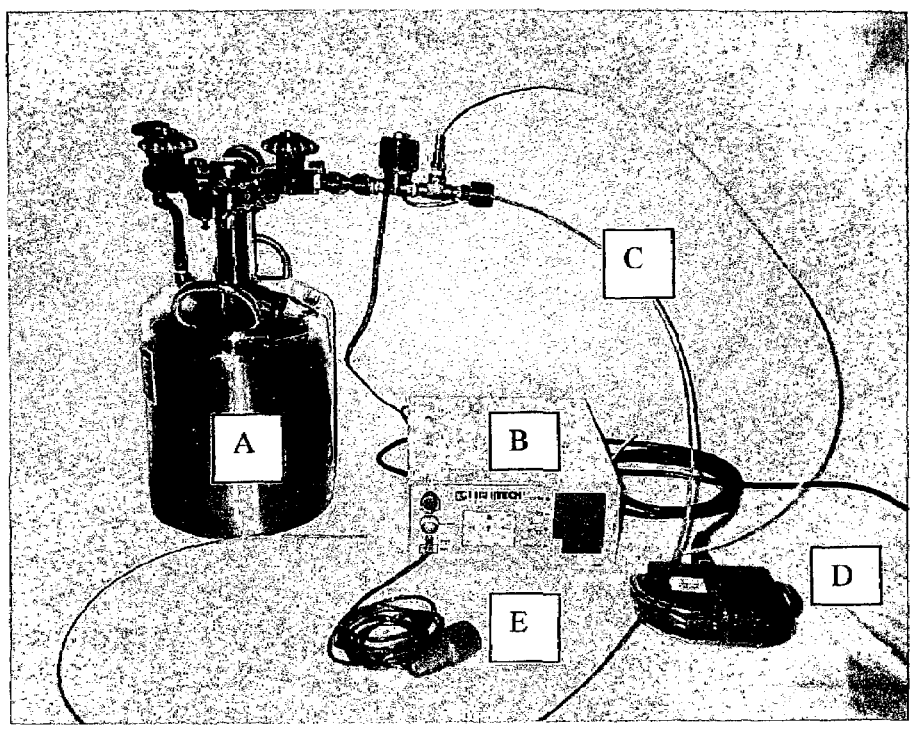
FIG. 29 is a photograph of the complete low pressure spray cryotherapy device.
Figure 30:
FIG. 30 is a photograph of an endoscope that can be used in cryotherapy.

With particular reference to FIGS. 8-11, the heated catheter in longitudinal cross section is shown with part of the hub base 43 broken away. Exemplary of the embodiment of this invention is an 84 inch PTFE basic catheter 18 which has an ⅛ inch groove 16 at the distal end 12 (FIGS. 7 and 8). The catheter 18 is etched (not shown) for bonding. With reference to FIGS. 9-11, a copper wire 28 runs the length of the catheter on the interior 24. The copper wire 28 runs out through a channel in the groove 16 and is folded over the distal end 12 of the catheter to the exterior 32 as best shown in FIG. 9. An ⅛ inch stainless sleeve 38 is press fit over the wire 28, covering the groove 16 completely and securely holding wire 28 in place. The proximal end 14 of the catheter 18 is flared 36 to 0.130" best shown in FIG. 7. Note particularly an insulating coating 31 covers the foil 22. This insulating coating extends only over a portion of the catheter and is covered by the parylene coating which covers the entire catheter. As shown in FIGS. 12-13, the wire exits the proximal end 14 of the catheter 18 and comes in contact with the post of the luer 37 and then the compression nut of the luer 39 is tightened, locking the catheter 18 and the wire 28 in place, as best shown in FIG. 27.

Note that a copper foil strip 22 is placed longitudinally at the proximal end 14 of the catheter 18. Referring to FIGS. 10 and 11 once the copper foil 22 is in place on the catheter 18 a short heat shrink insulating layer 31 goes from the hub base 40 to cover the copper foil (conductive strip) 22 and a short portion of the electrodag coating 30. The electrodag coating extends from a short portion on the copper foil to the distal end of the catheter and finally a parylene coating (dielectric insulator) covers the hub and catheter portions of the heated catheter, except for the female metal gas orifice 45 and hub contact pin 51. The electrodag coating is a conductive coating containing metal graphite and silver or any conductive material in an epoxy resin and is an integral part of the heated catheter. For purposes of this invention conductive strip 22 is copper, but any heat conductive material would be operative. The conductive strip 22 as disposed on the catheter has proximate end and a distal end. The distal end of conductive strip is in contact with the electrodag coating. The proximal end of the conducting strip is attached to wire 44 (best shown in FIG. 27). The conductive strip, the thin wire and electrodag coating when attached to the power source produce the heat for the catheter. In a typical example, the outer coating is heat shrink and will cover the entire foil section. As an example, the electrodag extends from the distal end of the foil, covering 1.5" of the foil, to the tip of the catheter, covering the stainless sleeve on the end of the catheter and is in turn covered with dielectric insulator 34.

Figure 16:
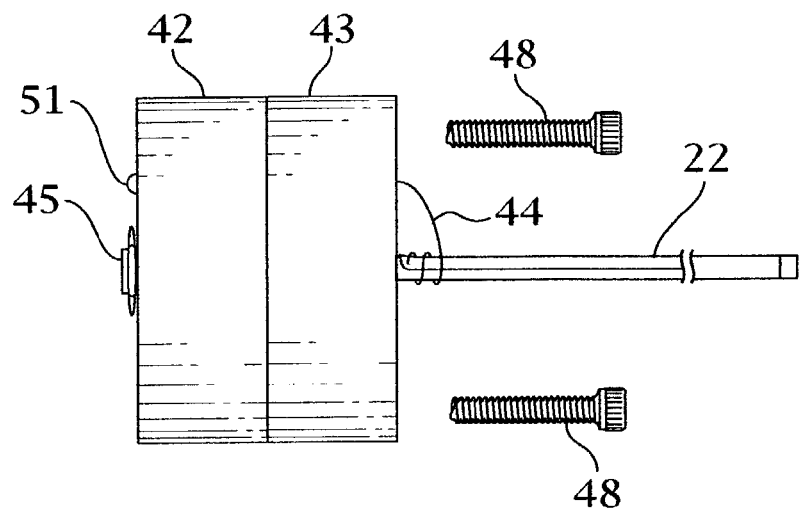
Figure 17:
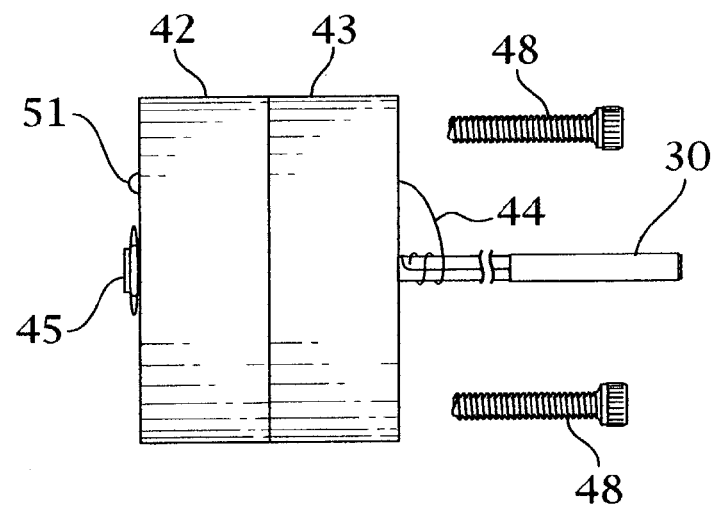
Figure 18:
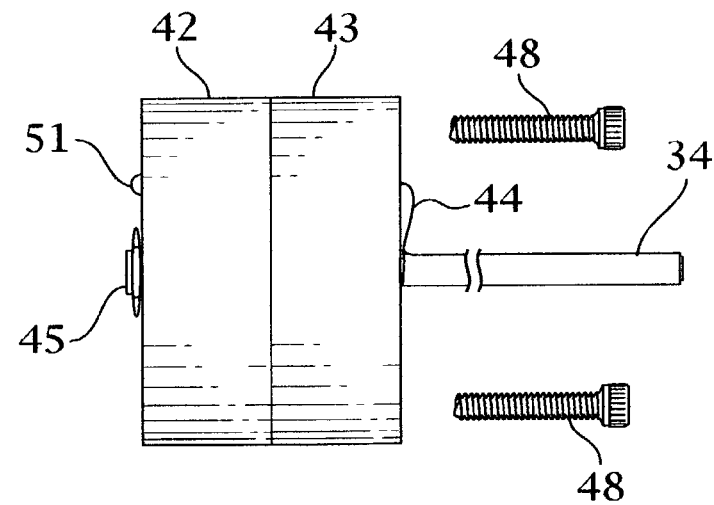

With particular reference to FIGS. 12-15, the manner for attaching the catheter 18 to the hub 40 is illustrated. FIG. 12 describes hub top 42 (in dashed lines) fixedly attached to the thread male portion 37 of the luer. In FIG. 12 there is illustrated a tube 47 having at its left end a gas intake orfice or luer 45, in its middle there is fixedly attached the male thread 37 and its right end there is a male catheter connector 49 which engages the flare 36 of the catheter in the female portion 39 of the compression nut. On tube 47 there is fixedly attached hub top 42 having gas intake orfice 45 and male luer 37 exposed. Specifically in assembling the catheter to the hub a wire 44 attached to copper foil 22 at the proximal end 14 of the catheter 18 the male end of tube 49 and female of luer 39 are joined and the wire is snugged tight in the luer as best shown in FIG. 27. Referring to FIGS. 14-16 the means for attaching wire 44 from the copper foil 22 to the post 46 attached to the internal portion of hub top 42 are shown. Note that wire 44 is attached at one end to the copper foil and runs from the copper foil through a channel in top 43 to attach to post 46 (e.g., by solder). Post 46 runs through the top of the base 42 to form post 51 which contacts electric ring 56 best described in FIG. 27. With reference to FIGS. 14-16, the top 42 and base 43 of the hub have hollow compartments 33 for retaining the luer.

Referring to FIGS. 15-18: At the proximal end of the catheter 18, an electrical wire 44 is soldered to the proximal end of the copper foil 22, the electrical wire 44 wraps a few times around the catheter 18 and enters the base of the hub 43, and through channel 35 to contact post 46 at the top of the hub 42. Note that contact post 46 extends through top 42 and becomes hub contact pin 51 which contacts ring 56 on hub connector 54 (described in detail in FIGS. 19-24). Electrical contact is made through metal luer and outside post.

As an example for assembling the heated catheter, 53 inches from the distal end 14 of the catheter 18 a short section of copper foil 22 runs along the exterior of the catheter 18 to the proximal end 14 and a connecting wire 44 runs from the copper foil through a channel 35 in the base 43 of the hub 40. Wire 44 attaches to the copper post 46 of the top section 42 of the hub 40 (FIG. 15). The copper post 46 is connected to a gold plated contact pin 51 on the surface of the hub 40. The base 43 mates to the top section 42 and is secured in place by two screws 48 (FIG. 16). The distal most 55 inches of the catheter is covered with electrodag coating 30, which covers all of the distal stainless steel hypodermic tube and two inches of the proximal foil (best shown in FIG. 10). Heat shrink coating 31 is applied 51 inches from the distal end and extends to the hub, completely covering the copper foil (FIG. 11). The Parylene or heat shrink coating covers the exterior of the catheter over the entire surface including the electrodag coating (FIG. 11). The outer coating is a dielectric or insulating coating. Advantageously, a Parylene film is used as the outer insulating coating because it can be formed in extremely thin layers. The flare 36 in the catheter tubing creates a positive fluid seal with the luer, while the hub 40 serves as the electrical connection for the wire on the interior of the catheter and from the foil 22 running the proximal length on the exterior of the catheter tubing. The interior of the hub houses a conductive material, while the outside of the hub is an insulator. The hub and the distal most portion of the catheter both maintain a zero potential electrically.

Figure 19:
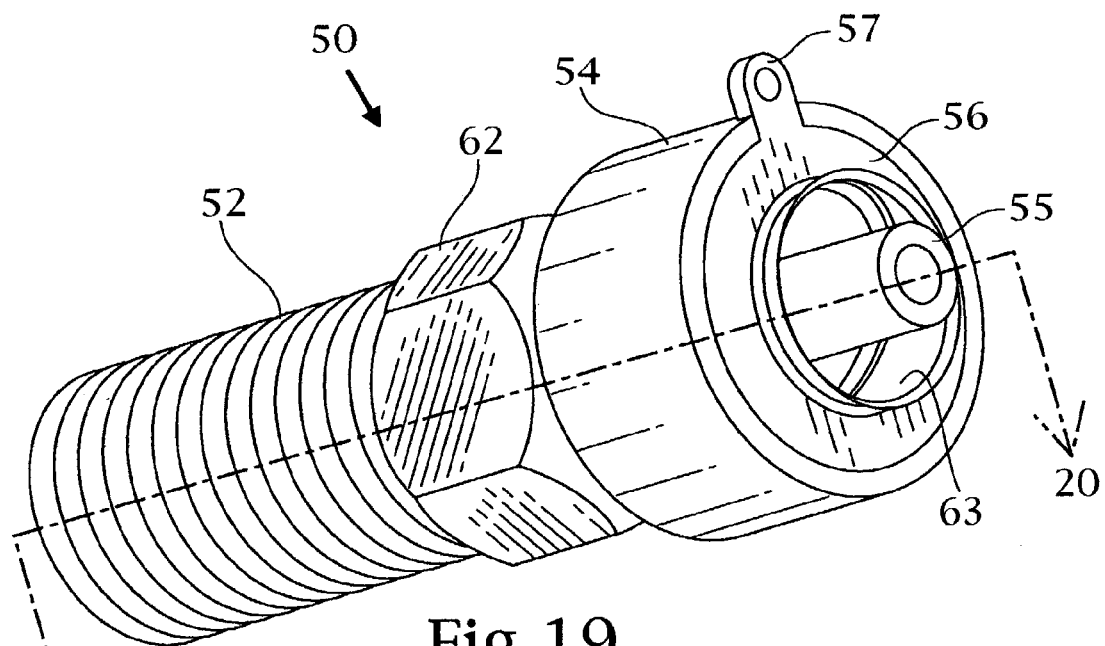
FIG. 19 is a perspective view of the gas and electric connector subassembly.
Figure 20:
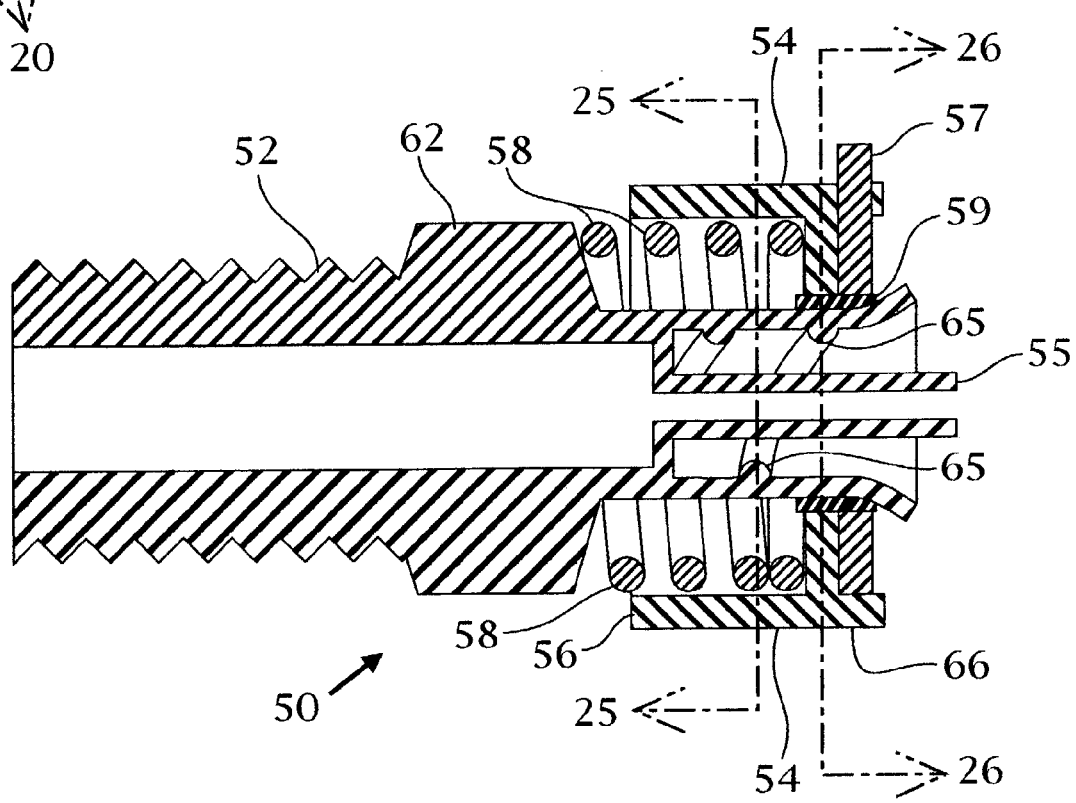
FIG. 20 is a cross-section thereof taken along lines 20-20 of FIG. 19.

With reference to FIGS. 19 and 20, there is shown the gas and electrical connection subassembly 50 having a gas connection threaded male gas nipple 52 for receiving the cryogenic gas. The gas nipple is joined at an end to a spring actuated hub connecting means 54 which contains a spring mechanism 58 for insuring a secure attachment. Referring specifically to FIGS. 19-20, the spring actuated hub connecting means 54 has a male member 55 for connecting to the female gas inlet 60 associated with top of the hub 42. Connector 54 also had therein an electric contact ring 56 for contacting pin 51 on the hub top 42, as well as a tab 57 on ring 56.

An important element of the electric and gas connection is the spring-loaded hub connector 54 shown in detail in FIGS. 20-24. Note that the hub connector has an internal spring 58 which is compressed by pushing on the sides of connector 54; connector 54 is joined to the female gas inlet 60 of the hub by inserting the male member 55 of connector 54 into female gas inlet 60, compressing the spring 58 in the connector by pushing on the side of the connector. While in the compressed state, male 55 and female 60 are jointed and tabs 64 on the female inlet 60 are inserted into threaded 65 annular opening 63 and turned a half turn so that the tabs 64 fully engage thread 65 as shown in FIGS. 21-24. Note particularly that in FIG. 21 springs 58 are not compressed; during engagement the spring 58 is compressed and upon engagement the spring 58 is released assuring a secure attachment. Tabs 64 are inserted into annular threaded opening 63; and the spring is released when tabs 64 and threads 64 are fully engaged. This spring loading insures a secure fit for both gas and electric connections. Note that the spring is retained in the hub connector 54 by abutting an end of the nipple 52 and housing 66.

Figure 21:
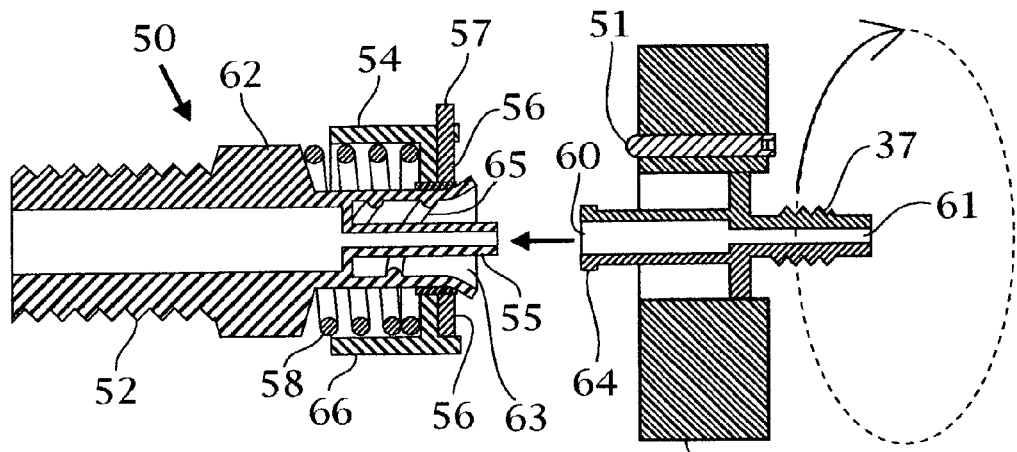
FIGS. 21-27 illustrate means by which the catheter is jointed to the gas and electric connector subassembly, with FIGS. 21-23 being longitudinal cross-sections of the gas and electric subassembly and top of the hub.
Figure 22:
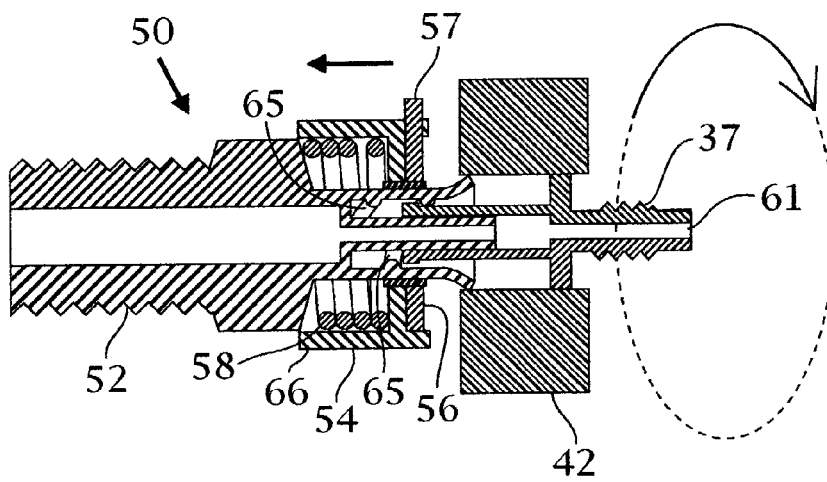
Figure 23:
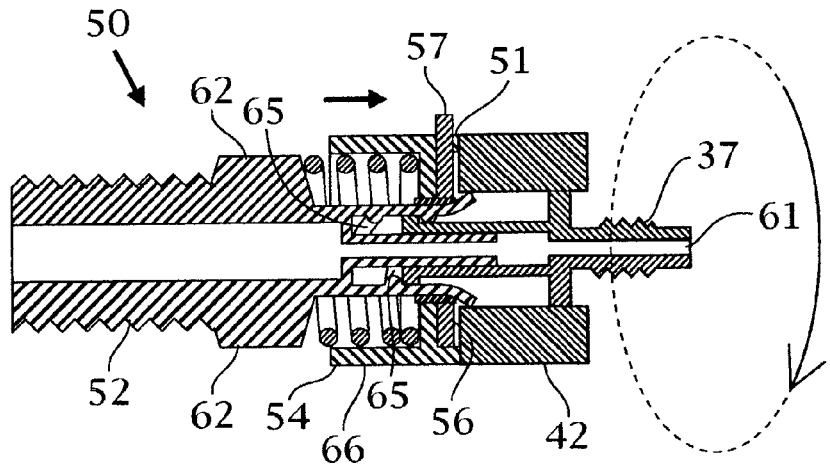
Figure 24:
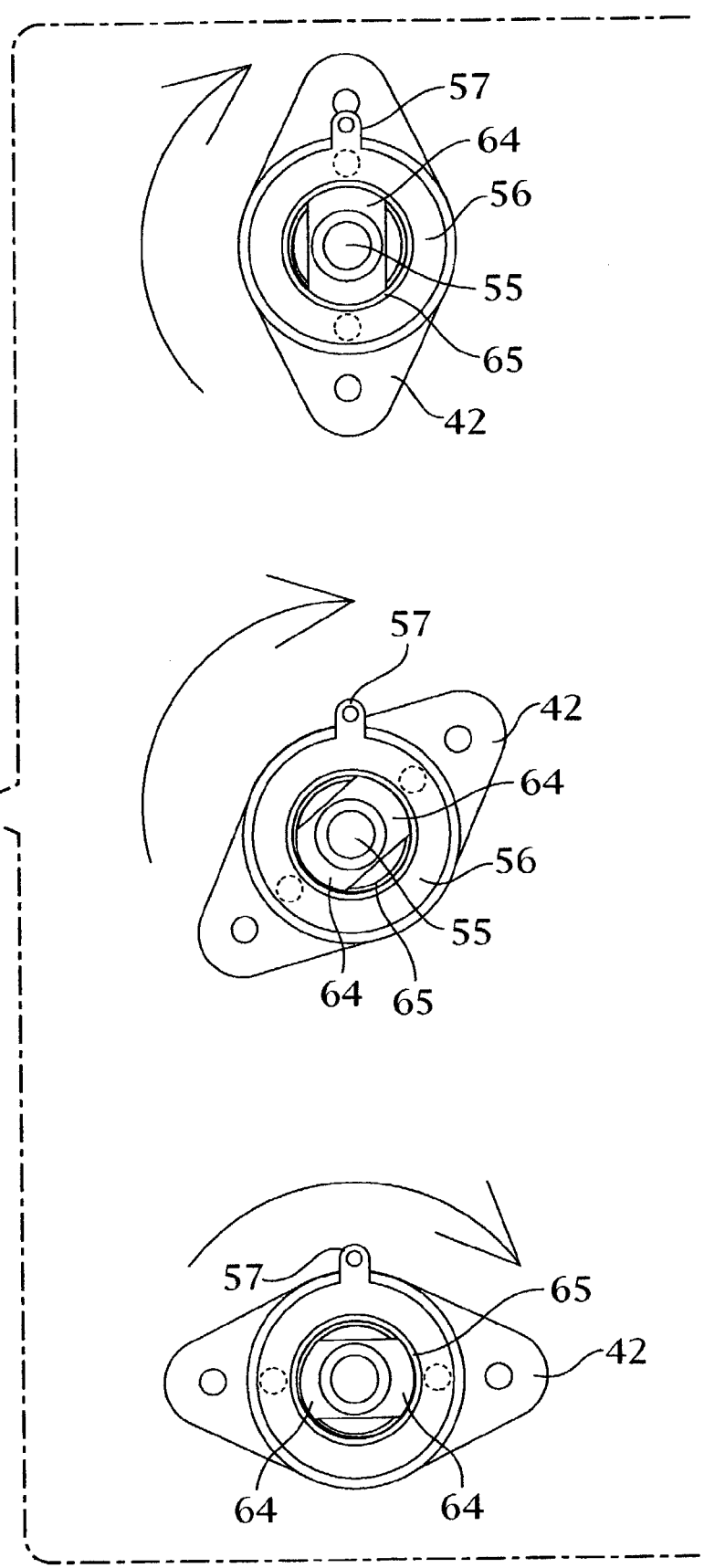

With reference to FIGS. 21-24, an elegant arrangement for securely joining the gas and electric subassembly 50 to the female gas inlet 60 of the hub top 42 is described. This joining depends upon tabs 64 on either side of female gas inlet 60 entering threaded annular opening 63. Once tab 64 enters said opening 63, the hub connector 54 is retracted, and tabs 64 are allowed to enter the threaded annular opening 63. The tabs 64 which are integral to hub 40 are turned by twisting the hub 40 a half of a turn so that the tabs 64 engage thread 65 in annular opening 63. Once the tabs 64 and thread 65 are engaged, hub connector 54 is released allowing spring 58 within the connector to fixedly attach the hub 40 to the hub connector 54. In FIGS. 21-23 the arrows are intended to illustrate the tabs 64 entering annular opening 63 to engage thread 65.

With reference to FIGS. 21-23, note also that the mating of the gas and electric subassembly 50 with the hub gas inlet 60 is described. On the opposite end of the gas inlet 60, there is a gas outlet 61 having disposed thereon the threaded member 37 of the luer. There is also fluid seal and electrical components for contacting the heating components of the catheter to the electric power supply.

Figure 25:
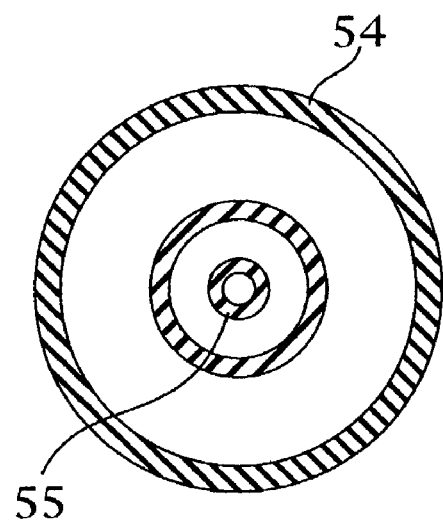
Figure 26:
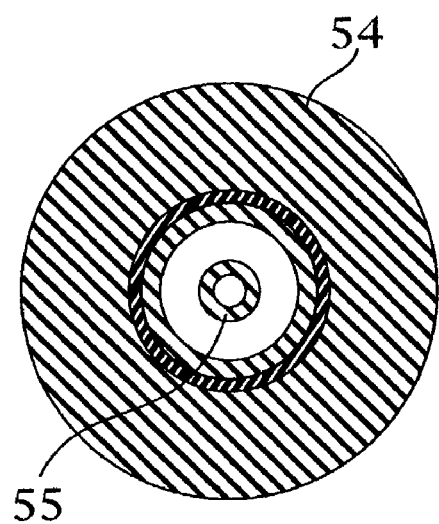

With reference to FIGS. 25 and 26, a cross section taken along lines 25-25 and 26-26 are described to show the male portion 55 of connector 54.

The male fitting connected the solenoid mates with the hub 40 to provide both a fluid seal and an electrical connection. The center of the fitting is the zero potential contact with the hub. On the outside of the male fitting, a compressed spring forces the proximal catheter contact to mate with the male connection.

The electric leads to heat the catheter are connected through electric tab 57 and the hex nut 62 of threaded nipple 52. The leads could be attached by soldering, clipping or other convenient means.

As an example, heating of the electrodag coating is achieved by applying 24 volts at 4.5-6 amps to the leads for 7 seconds, and then applying 12 volts at 3 amps for the remainder of the heating cycle which is indicated by the ability to remove the catheter from the endoscope (approximately 13-15 seconds depending on the cryo-treatment exposure time). No negative effects will occur if the heater is applied longer than these time frames. The resistance of the electrodag generates heat as the current is passed through the length of the catheter. The initial 24 volts provide a quick initial thaw, while the remaining heating phase maintains and finishes the thaw cycle. All materials maintain all structural and functional properties through the entire heating cycle.

The herein disclosed invention has been described in terms of a catheter with an electrodag coating, however, other electrical means such as a conductive powder coating, a catheter made of conductive plastic or the like or metal would be operative.

In a broad aspect, the herein disclosed invention envisions a heated catheter in combination with an endoscope, with the heated catheter being fitted into a lumen of the endoscope.

Following a treatment cycle, the catheter may be warmed by depressing the right side of the foot pedal. A light on the solenoid will indicate that the catheter is experiencing a thaw cycle. The cycle can be interrupted at any time by releasing the foot pedal. Heat is generated by the resistance in the electrodag coating applied to the outer surface of the catheter. The hub has two contacts. The internal contact extends from the hub, through the catheter's internal surface to the distal fitting by means of the internal copper wire. This lead maintains a zero potential at all times. The second contact is located on the top surface of the hub. This contact extends from the hub, through the copper foil along the exterior of the catheter and into the proximal electrodag coating.

Advantages of the Heated Catheter

The heated catheter provides a number of advantages over a traditional catheter:

Polyimide or PTFE, the Cryo-catheter material base, acts as a strong insulator and transports the liquid nitrogen with minimal thermal temperature loss resulting in a shorter time to achieve the clinically required cryoburn.

The heating mechanism allows the catheter to be removed from the endoscope lumen immediately following the cryo-therapy. More specifically, using a traditional catheter, the catheter is frozen into the endoscope lumen for 1-5 minutes following the therapy. This freezing to the endoscope lumen may result in damage to the endoscope.

Insulated Fittings

The new fittings on the device will be vacuum insulated. This will keep the fittings from frosting or feeling super cool to the human touch.

In addition, the hub or connective fittings which couple the catheter to the cryosystem have been redesigned and improved to accommodate electrical contacts required for the heating system.

Alternative Embodiments of the Heated Catheter

An alternative embodiment contemplated by the inventors is a heating coil on the heated catheter being energized in "series" or heated with a continuous length of wire energized from two ends. Also contemplated is a catheter with the heating element in parallel. This will result in heating short segments (5-10 segments per catheter) quickly and with more energy. The inventors may adjust the wrappings of the heating coil so that the loops touch one another. A parallel electrical transfer may be necessary. It may be feasible to employ flat wire (square wire) as opposed to round wire. Whether to use series or parallel spacing will be determined based on individual use. The inventors contemplate coating the gap between the wires with a heat sink which will act to absorb radiated heat from the heating coil to dispense the heat to the outside of the catheter. Also contemplated by the inventors is a spray coat or liquid paint of a nichrome conductor. In this embodiment the entire catheter could be energized quite quickly. The inventors envision alternate means for diverting freezing temperatures from non-target areas. Examples of such diverting means is a polystyrene tape to function as an insulator. Alternatively, the catheter may be made of polystyrene or some other insulating material. During the cryoburn the heat of the catheter remains active. This prevents the accidental injury to non-target tissue.

The inventors have produced a further alternative embodiment of a heated catheter. The heated catheter in the alternative embodiment is a composite constructed of three different materials; in three different layers. The catheter itself (as the first layer) is made of extruded polyimide. Surrounding the first layer (the catheter) is a layer of magnetic wire wrapped around the outer diameter of the polyimide catheter. As a top or final layer, there is supplied a thin polyester heat shrink.

More specifically, the heated catheter (cryocatheter) can be defined as an extruded polyimide tube (O.D. 0.092"). Over the catheter is wrapped a layer of magnetic copper wire (0.007" diameter). A number of different diameter wires are available. The inventors put together prototypes with 0.003" diameter wire, 0.002" diameter wire, 0.005" diameter wire, etc. A 0.007" diameter wire was the best for the desired voltage, but the invention does not exclude the use of wires of other diameters.

The wrappings of wire that functioned the best were 8 wraps per inch (a single strand was run the length of the catheter, and the wrapping was applied back over this single strand to complete the electrical loop. Double strand wrapping with the wrap spacing (up to 25 wraps per inch) would be operative.

A selected preferred voltage for application is 12 volts and 1 amp. Voltages of 5, 12, 17 and 24 volts have been tested. The important thing to keep in mind is that different diameter wires work well if wrapped to the correct density and heated with the appropriate amount of voltages.

The final layer employed is a thin (0.00025") polyester heat shrink. This heat shrink serves to hold the wire in place and to seal the wire from patient contact.

As an elegant embodiment of this invention, the heated catheter is disposable (e.g., single-use) and can be used together with an en endoscope to perform cryosurgical procedures in the esophagus and as such the catheter will not be allowed to freeze to the endoscope.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A catheter for use with an endoscope in a cryosurgical procedure, the catheter comprising:

an elongated tubular member having a length at least as long as the working length of said endoscope and having an inside for conveying cryogen from a proximal end to a distal end, and an outside, the distal end being open and adapted to spray cryogen at low temperature and low pressure at selected target tissue; and a heating element disposed longitudinally on at least a portion of the outside of the tubular member for heating at least a portion of the length of the catheter;

the outer diameter of the combined tubular member and heating element being smaller than the diameter of a lumen of an endoscope.

2. The catheter of claim 1 further comprising a dielectric insulator disposed about the heating element.

3. The catheter of claim 2 wherein, the dielectric insulator is concentrically disposed about the heating element, and wherein the outer diameter of the combined tubular member, heating element and dielectric insulator is smaller than the diameter of a lumen of an endoscope such that the catheter can be manipulated within the endoscope to spray cryogen at selected target tissue.

4. The catheter of claim 1 wherein, the heating element comprises an electrically conductive material.

5. The catheter of claim 4 wherein, the electrically conductive material is flexible, such that the catheter can be manipulated relative to an area being ablated during delivery of the cryogen.

6. The catheter of claim 1 wherein, the portion of the catheter adjacent the heating element, including the tubular member, consists essentially of a low pressure material.

7. The catheter of claim 6 wherein, the low pressure material is polytetrafluoroethylene, polyimide or a material that can withstand about the same pressure range as polytetrafluoroethylene or polyimide.

8. The catheter of claim 6 wherein, the portion of the catheter adjacent the heating element, including the tubular member, is not designed to withstand pressure greater than about 200 psi.

9. The catheter of claim 6 wherein, the portion of the catheter adjacent the heating element, including the tubular member, is not designed to withstand pressure greater than about 45 psi.

10. The catheter of claim 1 wherein, the heating element is disposed over substantially the entire length of the tubular member that, in use, is within the lumen of the endoscope.

11. The catheter of claim 1 wherein, the outer diameter of the combined tubular member and heating element is about 4 mm or less.

12. The catheter of claim 1 wherein, the outer diameter of the combined tubular member and heating element is about 3 mm or less.

13. The catheter of claim 1 wherein, the outer diameter of the combined tubular member and heating element is smaller than a lumen of 2.8 mm.

14. The catheter of claim 1 wherein, the tubular member is at least as long as an endoscope having a working length of 104 cm.

15. A catheter for use in a cryosurgical procedure, the catheter comprising:
   a tubular member having an inside surface defining a channel for cryogen flow, a proximal end for receiving cryogen from a cryogen source, and a distal end, the distal end being open and adapted to spray low temperature, low pressure cryogen at target tissue, the inside surface of at least the distal end comprising a low pressure material; and
   a heating element disposed longitudinally along at least a portion of the length of the tubular member;
   the combined tubular member and heating element being sized to fit within a lumen of an endoscope.

16. The catheter of claim 15 wherein, the low pressure material is a polymer.

17. The catheter of claim 15 wherein, the low pressure material comprises polytetrafluoroethylene, polyimide or a material that can withstand about the same pressure range as polytetrafluoroethylene or polyimide.

18. The catheter of claim 15 wherein, the outer diameter of the combined tubular member and heating element are smaller than the diameter of the lumen such that the catheter can be manipulated within the endoscope to spray cryogen at selected target tissue.

19. The catheter of claim 15 wherein, the inside surface of the tubular member is not designed to withstand pressure greater than about 200 psi.

20. The catheter of claim 15 wherein, the inside surface of the tubular member is not designed to withstand pressure greater than about 45 psi.

21. The catheter of claim 15 wherein, the catheter consists essentially of the tubular member, the heating element and a dielectric insulator disposed about the heating element.

22. A catheter for use with an endoscope in a cryosurgical procedure, the catheter comprising:
   a tubular member having a proximal end for receiving cryogen, an open distal end adapted to spray low temperature, low pressure cryogen at target tissue, an outside surface, and an inside surface, the inside surface comprising an insulating polymer that defines a channel and, in use, contacts cryogen flowing from the proximal end to the distal end; and
   a heating element disposed longitudinally along at least a portion of the outside surface.

23. The catheter of claim 22 wherein, the catheter consists essentially of the tubular member, the heating element and a dielectric insulator disposed about the heating element.

24. The catheter of claim 22 wherein, the insulating polymer comprises polytetrafluoroethylene, polyimide or a material that can withstand about the same pressure range as polytetrafluoroethylene or polyimide.

25. The catheter of claim 22 wherein, the outer diameter of the combined tubular member and heating element are smaller than a diameter of a lumen of the endoscope such that the catheter can be manipulated within the endoscope to spray cryogen at selected target tissue.

26. The catheter of claim 22 wherein, the insulating polymer is selected from the group consisting of polytetrafluoroethylene, polyimide and polystyrene.

27. A cryosurgical apparatus for cryogenic spray ablation, comprising a catheter having an elongated tubular member with a length, an inside for conveying cryogen from a proximal end to a distal end, and an outside, the distal end being open and adapted to spray cryogen at selected target tissue, a source of cryogen attached to the catheter by a conduit, and a heating element disposed longitudinally on at least a portion of the outside of the tubular member for heating at least a portion of the length of the catheter, wherein the apparatus is configured such that, in use, cryogen exits the catheter distal end at low temperature and low pressure.

* * * * *